US005487984A

United States Patent [19]
Allet et al.

[11] Patent Number: 5,487,984
[45] Date of Patent: * Jan. 30, 1996

[54] PROCESSES FOR PRODUCING TUMOR NECROSIS FACTOR

[75] Inventors: Bernard Allet, Onex; Eric H. Kawashima, Geneva, both of Switzerland

[73] Assignee: Biogen, Inc., Cambridge, Mass.

[*] Notice: The portion of the term of this patent subsequent to Jan. 26, 2010, has been disclaimed.

[21] Appl. No.: 811,654

[22] Filed: Dec. 20, 1985

Related U.S. Application Data

[63] Continuation-in-part of Ser. No. 684,595, Dec. 21, 1984, abandoned, and Ser. No. 785,847, Oct. 9, 1985, abandoned.

[51] Int. Cl.$^6$ ............................ C12N 15/00; C12N 15/19
[52] U.S. Cl. ................ 435/69.5; 435/320.1; 435/254.11; 435/252.33; 536/23.5; 536/24.1
[58] Field of Search ................................ 435/68, 70, 71, 435/253, 320, 172.3; 935/6, 9–11, 13, 22, 23, 27, 29, 38, 47, 55, 56, 60, 61, 73, 72; 536/27

[56] References Cited

U.S. PATENT DOCUMENTS

| | | |
|---|---|---|
| 4,309,418 | 1/1982 | Green . |
| 4,677,064 | 6/1987 | Mark et al. ............................ 530/351 |
| 4,677,663 | 6/1987 | Mark et al. ............................ 530/351 |
| 4,871,663 | 10/1089 | Ohima et al. ........................ 435/172.3 |
| 4,879,226 | 11/1989 | Wallace et al. ...................... 435/240.2 |
| 4,880,915 | 11/1989 | Kajihara et al. ........................ 530/415 |
| 5,182,196 | 1/1993 | Allet et al. ............................ 435/69.5 |

FOREIGN PATENT DOCUMENTS

WO8401288  4/1984  WIPO .

OTHER PUBLICATIONS

G. R. Adolf and I. Fogy, "Purification And Characterization Of A Cytotoxic Human Protein (Lymphotoxin/Tumor Necrosis Factor)", 4th International Lymphokine Workshop, *Lymphokine Res.*, 3(4), p. 231 (1984).

N. Bloksma et al., "Endotoxin–Induced Release Of Tumour Necrosis Factor And Interferon In Vivo Is Inhibited By Prior Adrenoceptor Blockade," *Cancer Immunol Immunother*, 14, pp. 41–45 (1982) (Bloksma I).

N. Bloksma et al., "Antitumour Activity Of Endotoxin, Concanavalin A and poly I:C And Their Ability To Elicit Tumour Necrosis Factor, Cytostatic Factors, And Interferon In Vivo," *Cancer Immunol Immunother*, 16, pp. 35–39 (1983) (Bloksma II).

E. A. Carswell et al., "An Endotoxin–Induced Serum Factor That Causes Necrosis of Tumors," *Proc. Natl. Acad. Sci. USA*, 72, pp. 3666–3670 (1975).

G. A. Currie and C. Basham, "Activated Macrophages Release A Factor Which Lyses Malignant Cells But Not Normal Cells," *J. Exp. Med.*, 142, pp. 1600–1605 (1975).

G. A. Currie, "Activated Macrophages Kill Tumor Cells By Releasing Arginase", *Nature*, 273, pp. 758–759 (1978).

N. Fiore et al., "Tumor Necrosis Factor: Further Studies," *Proc. Am. Assoc. Cancer Res.* (Abstract 498), 16, p. 125 (1975).

N. Freudenberg et al., "Haemorrhagic Tumor Necrosis Following Endotoxin Administration," *Virchows Arch*, 403, pp. 377–389 (1984).

F. de–Germain Matteis and G. R. Burleson, "Comparison And Characterization Of Gamma Interferon And Tumor Necrosis Factor In The Rat System," *Fed. Proc.*, 41(3), Abst. 1012 (1982).

S. Green et al., "Mechanism of Endotoxin–Induced Tumor Hemorrhagic Necrosis," *AACR Abstracts* (Abstract 554), 15, p. 139 (1974).

S. Green et al., "Partial Purification of a Serum Factor That Causes Necrosis of Tumors," *Proc. Nat. Acad. Sci. USA*, 72, pp. 381–385 (1976).

S. Green et al., "Necrosis of Meth A tumors by a Factor From Liver of C. parvum (CP) Endotoxin–Treated Mice," (Abstract) *AACR Abstracts* (Immunology) 17, p. 84 (1976).

**S. Green et al., "Evidence For The Presence Of An Antitumor Factor In Serum Of Normal Aminals", *Cancer Letters*, 6, pp. 235–240 (1979).

S. Green et al. "Action Of Tumor Necrosis Factor (TNF) On Mouse Myelomonocytic Leukemia (WEHI/3) In Vitro And In Vivo," *AACR Abstracts* (Immunology) p. 294 (1981).

S. Green et al., "Murine Tumor Necrosis–Inducing Factor: Purification And Effects On Myelomonocytic Leukemia Cells," *JNCI*, 68, pp. 997–1003 (1982).

J. Hammerstrøm, "Soluble Cytostatic Factor(s) Released from Human Monocytes: I. Production and Effect on Normal and Transformed Human Target Cells," *Scand. J. Immunol.*, 15, pp. 311–318 (1982).

C. G. Haidaris et al., "Serum Containing Tumor Necrosis Factor Is Cytotoxic For The Human Malaria Parasite *Plasmodium falciparum,*" *Infection and Immunity*, 42, pp. 385–393 (1988).

K. Haranaka and N. Satomi, "Note: Cytotoxic Activity of Tumor Necrosis Factor (TNF) on Human Cancer Cells in vitro," *Japan J. Exp. Med.*, 51, pp. 191–194 (1981).

K. Haranaka et al., "Antitumor Activity Of Murine Tumor Necrosis Factor (TNF) Against Transplanted Murine Tumors And Heterotransplanted Human Tumors In Nude Mice," *Int. J. Cancer*, 34, pp. 263–267 (1984).

(List continued on next page.)

Primary Examiner—Marianne P. Allen
Attorney, Agent, or Firm—Fish & Neave; James F. Haley, Jr.; Margaret A. Pierri

[57] ABSTRACT

A process of producing mammalian tumor necrosis factors (TNF) and TNF-like polypeptides by culturing eukaryotic or prokaryotic hosts transformed with DNA sequences encoding those polypeptides. A process for purifying TNF-like polypeptides using an anion exchanger. The TNFs and TNF-like polypeptides produced by the processes of this invention, and compositions and methods utilizing those TNFs and TNF-like polypeptides, are useful in anticancer, antitumor and antimalarial therapies. They are also useful together with interferon therapy, chemotherapy in anticancer and antitumor therapies, and in combination with actinomycin D in the treatment of tumor-bearing mammals.

11 Claims, 21 Drawing Sheets

OTHER PUBLICATIONS

K. Haranaka et al., "Differences In Tumour Necrosis Factor Productive Ability Among Rodents," *Br. J. Cancer*, 50, pp. 471–478 (1984).

K. Haranaka et al., "Role of First Stimulating Agents In The Production Of Tumor Necrosis Factor," *Cancer Immunol Immunother*, 18, pp. 87–90 (1984).

L. Helson et al., "Effects of Murine Tumour Necrosis Factor on Cultured Human Melanoma Cells," *Nature* (London), 258, pp. 731–732 (1975).

L. Helson et al., "Effect of Tumor Necrosis Factor on Heterotransplanted Human Tumors," *Exp. Cell Biol.*, 47, pp. 53–60 (1979).

J. B. Hibbs, Jr., "The Macrophage As A Tumoricidal Effector Cell: A Review of In Vivo and In Vitro Studies On The Mechanism Of The Activated Macrophage Nonspecific Cytotoxic Reaction", in *The Macrophage In Neoplasia*, ed. M. A. Fink, pp. 83–111 (1976).

M. K. Hoffmann et al., "Serum Containing Endotoxin–Induced Tumour Necrosis Factor Substitutes For Helper T–Cells," *Nature*, 263, pp. 416–417 (1976).

M. K. Hoffmann et al., "Endotoxin–induced Serum Factor Controlling Differentiation of Bone Marrow Derived Lymphocytes", *Proc. Natl. Acad. Sci. USA*, 74, pp. 1200–1203 (1977).

M. K. Hoffmann et al., "Induction and Immunological Properties of Tumor Necrosis Factor", *J. Reticuloendothelial. Soc.*, 23, pp. 307–319 (1978).

A. Itoh et al., "Induction Of TNF–like Factor By Murine Macrophage–like cell line J774.1 On Treatment With *Sarcophaga lectin,*" *FEBS*, 175, pp. 59–62 (1984).

N. Kiger et al., "Tumor–Necrotizing Serum Production By Administration Of BCG+Pseudomonas: Its Application In Treatment Of Fibrosarcoma In Mice," *Recent Results Cancer Res.*, 75, pp. 220–225 (1980).

R. G. Kilbourn et al., "Activated Macrophages Secrete A Soluble Factor That Inhibits Mitochondrial Respiration Of Tumor Cells," *Journal Of Immunology*, 133, pp. 2577–2581 (1984).

F. C. Kull, Jr. and P. Cuatrecasas, "Possible Requirement of Internalization in the Mechanism of In Vitro Cytotoxicity in Tumor Necrosis Serum," *Cancer Research*, 41, pp. 4885–4890 (1981).

F. C. Kull, Jr. and P. Cuatrecasas, "Preliminary characterization Of The Tumor Cell Cytotoxin In Tumor Necrosis Serum," *Journal Of Immunology*, 126, pp. 1279–1283 (1981).

D. N. Männel et al., "Generation And Characterization Of A Lipopolysaccharide–Induced and Serum–Derived Cytotoxic Factor For Tumor Cells", *Infect. Immun.*, 28, pp. 204–211 (1980).

D. N. Männel et al., "Macrophages as a Source of Tumoricidal Activity (Tumor Necrotizing Factor)," *Infection and Immunity*, 30, pp. 523–530 (1980).

D. N. Männel et al., "Inhibition Of Nonspecific Tumoricidal Activity By Activated Macrophages With Antiserum Against A Soluble Cytotoxic Factor," *Infection and Immunity*, 33, pp. 156–164 (1981).

N. Matthews and J. F. Watkins, "Tumour–Necrosis Factor From The Rabbit. I. Mode of Action, Specificity and Physicochemical properties", *Br. J. Cancer*, 38, pp. 302–309 (1978).

N. Matthews, "Tumour Necrosis Factor From The Rabbit. II. Production By Monocytes", *Br. J. Cancer*, 38, pp. 310–315 (1978).

N. Matthews, "Tumor–Necrosis Factor From The Rabbit. III. Relationship To Interferons," *Br. J. Cancer*, 40, pp. 534–539 (1979).

N. Matthews et al., "Tumour Necrosis Factor From The Rabbit. IV. Purification And Chemical characterization," *Br. J. Cancer*, 42, pp. 416–422 (1980).

N. Matthews, "Tumour Necrosis Factor From The Rabbit. In Vivo Activity And Sites Of Synthesis," *Br. J. Cancer*, 44, p. 294 (1981).

N. Matthews, "Production of an Anti–Tumour Cytotoxin By Human Monocytes," *Immunology*, 44, p. 135 (1981).

N. Matthews, "Production of an Anti–Tumor Cytotoxin by Human Monocytes: Comparison of Endotoxin, Interferons and Other agents as Inducers," *Br. J. Cancer*, 45, pp. 615–617 (1982).

N. Matthews, "Anti–tumour Cytotoxin From Macrophages: No Correlation Between Cytotoxin Adsorption By Tumour Cell Lines And Their Cytotoxin Susceptibility," *Immunology*, 53, pp. 537–543 (1984).

M. S. Meltzer and Gerald L. Bartlett, "Cytotoxicity in vitro by Products of Specifically Stimulated Spleen Cells: Susceptibility of Tumor Cells and Normal Cells," *J. Natl. Cancer Inst.*, 49, p. 1439 (1972).

M. Mihara et al., "Immunopharmacological Study On Tumor Necrosis Factor," *Jpn. J. Pharmacol.*, 36, 49P (1984).

M. Lynne Neale and N. Matthews, "Antimicrobial Effects Of A Macrophage–Derived Cytotoxin From The Serum Of BCG–Prime Rabbits (Tumour Necrosis Serum)" *Med. Microbiol.*, 17, pp. 211–213 (1984).

H. F. Oettgen et al., "Endotoxin–Induced Tumor Necrosis Factor," *Recent Results in Cancer Research.*75. *Cancer Chemo– And Immuno–pharmacology*, pp. 207–212 (1980).

L. J. Old, "Tumor Necrosis Factor," *Clinical Bulletin*, 6, pp. 118–120 (1976).

L. Old, "Cancer Immunology: The Search for Specificity—G. H. A. Clowes Memorial Lectures" *Cancer Research*, 41, pp. 361–375 (1981).

H. G. Opitz et al., "Inhibition of a $^3$H–Thymidine Incorporation of Lymphocytes by a Soluble Factor from Macrophages," *Cell. Immunol.*, 16, pp. 379–388 (1975).

J. M. Ostrove and G. E. Gifford, "Stimulatin Of RNA Synthesis in L–929 Cells By Rabbit Tumor Necrosis Factor," *Proceedings Of The Society For Experimental Biology And Medicine*, 160, pp. 354–358 (1979).

M. Parant, "Antimicrobial Resistance Enhancing Acitivity Of Tumor Necrosis Serum Factor Induced By Endotoxin In BCG–Treated Mice," *Recent Results Cancer Res.*, 75, pp. 213–219 (1980).

V. J. Pasanen, "In Vitro Enhancement of Natural Cytotoxicity—by Tumour Necrosis Serum," *Scand. J. Immunol.*, 10, pp. 281–284 (1979).

W. F. Piessens et al., "Macrophages Activated In Vitro with Lymphocyte Mediators Kill Neoplastic But Not Normal Cells." *J. Immunol.*, 114, pp. 293–299 (1975).

J. H. L. Playfair et al., "Endotoxin Induced 'Tumour–Necrosis Serum' Kills A subpopulation Of Normal Lymphocytes In Vitro", *Clin Exp. Immunol.*, 47, pp. 753–755 (1982).

M. R. Ruff and G. E. Gifford, "Purification And Physico–Chemcial Characterization Of Rabbit Tumor Necrosis Factor" *Journal of Immunology*, 125, pp. 1671–1677 (1980).

M. R. Ruff and G. E. Gifford, "Rabbit Tumor Necrosis

Factor: Studies Concerned With The Mechanism Of Action," *Abst. Ann. Meeting Am. Soc. Microbiol.,* 80 (1980).

M. R. Ruff and G. E. Gifford, "Rabbit Tumor Necrosis Factor: Mechanism Of Action", *Infection and Immunity,* 31, pp. 380–385 (1981).

N. Satomi et al., "Research On The Production Site Of Tumor Necrosis Factor (TNF)," *Japan J. Exp. Med.,* 51, pp. 317–322 (1981).

C. C. Stewart et al., "Interaction of Macrophages with Tumor Cells," *Adv. Exp. Med. Biol.,* 73B, pp. 423–433 (1976).

K. Suyama et al., "Action of Tumor Necrosis Factor (TNF) On Friend Erythroleukemic Cells In Vitro," *Fed. Proc.,* 41(3), Abstract 2408 (1982).

J. Taverne et al., "Endotoxin–Induced Serum Factor Kills Malarial Parasites In Vitro," *Infection And Immunity,* 33, pp. 83–89 (1981).

PURIFICATION OF RABBIT-TNF FROM SERUM (50 RABBITS)

FIG. 4

TNF FRAGMENT 3

MetLysLeuThrAspAsnGlnLeuValValProAlaAspGlyLeuTyrLeuIleTyr
ATGAARCTNACNGAYAAYCARCTNGTNGTNCCNGCNGAYGGNCTNTAYCTNATYTAY
   TTR      TTR          TTR   TTRATA

| | |
|---|---|
| 3'-TTYAAYTGNCTRTTRGTYGANCANCANGGNCG-5' | RAB TNF3-I |
| 3'-TTYGANTGNCTRTTRGTYGANCANCANGGNCG-5' | RAB TNF3-II |
| 3'-TTYAAYTGNCTRTTRGTYAAYCANCANGGNCG-5' | RAB TNF3-III |
| 3'-TTYGANTGNCTRTTRGTYAAYCANCANGGNCG-5' | RAB TNF3-IV |

```
|          TNF3-1                        |         TNF3-2           |
ATGAAACTMACMGACAACCAACTMGTMGTMCCMGCMGACGGMCTMTACCTMATMTAC
TACTTTGAKTGKCTGTTGGTTGAKCAKCAKGGKCGKCTGCCKGAKATGGAKTAKATGTAA
|          TNF3-3           |         TNF3-4           |
```

TNF FRAGMENT 4

```
MetAlaTrpTyrGluProIleTyrLeuGlyGlyValPheGlnLeuGluLysGlyAspArgLeu
ATGGCNTGGTAYGARCCNATYTAYCTNGGNGGNGTNTTYCARCTNGARAARGGNGAYCGNCTN
         ATA     TTR               TTR          AGRTTR
```

```
3'-ACCATRCTYGGATADATRRA-5'       RAB TNF4-A1
   ACCATRCTYGGGTADATRRA          RAB TNF4-A2
   ACCATRCTYGGCTADATRRA          RAB TNF4-A3
   ACCATRCTYGGTTADATRRA          RAB TNF4-A4

ACCATRCTYGGGTAAATRRA          RAB TNF4-A2-1
   ACCATRCTYGGGTAGATRRA          RAB TNF4-A2-2
   ACCATRCTYGGGTATATRRA          RAB TNF4-A2-3
```

```
                    3'-AARGTYAACCTYTTYCCXCT-5'    RAB TNF4-B1
                       AARGTYAATCTYTTYCCXCT       RAB TNF4-B2
                       AARGTYGAACTYTTYCCXCT       RAB TNF4-B3
                       AARGTYGAGCTYTTYCCXCT       RAB TNF4-B4
                       AARGTYGACCTYTTYCCXCT       RAB TNF4-B5
                       AARGTYGATCTYTTYCCXCT       RAB TNF4-B6
```

```
|       TNF4-1          ||        TNF4-2           |
 TGGTACGAACCMATMTACCTMGGCGGCGTCTTCCAACTMGAAAAAGGMGACAGT
 ACCATGCTTGGKATKATGGTKCCGCCGCAGAAGGTTGAKCTTTTTCCKCTGTCATTAA
|        TNF4-3              ||          TNF4-4            |
```

NUCLEOTIDE SEQUENCE OF MOUSE TNF cDNA

```
1    CCTCAGCGAGGACAGCAAGGGACTAGCCAGGAGGGAGAACAGAAACTCCAGAACATCCTG  60

61   GAAATAGCTCCCAGAAAAGCAAGCAGCCAACCAGGCAGGTTCTGTCCCTTTCACTCACTG  120

121  GCCCAAGGCGCCACATCTCCCTCCAGAAAAGACACO ATG AGCACAGAAAGCATGATCCGC  180
                                          M   S   T   E   S   M   I   R

181  GACGTGGAACTGGCAGAAGAGGCACTCCCCCAAAAGATGGGGGGCTTCCAGAACTCCAGG  240
      D   V   E   L   A   E   E   A   L   P   Q   K   M   G   G   F   Q   N   S   R

241  CGGTGCCTATGTCTCAGCCTCTTCTCATTCCTGCTTGTGGCAGGGGCCACCACGCTCTTC  300
      R   C   L   C   S   L   F   S   F   L   L   V   A   G   A   T   T   L   F

301  TGTCTACTGAACTTCGGGGTGATCGGTCCCCAAAGGGATGAGAAGTTCCCAAATGGCCTC  360
      C   L   L   N   F   G   V   I   G   P   Q   R   D   E   K   F   P   N   G   L

361  CCTCTCATCAGTTCTATGGCCCAGACCCTCACACTCAGATCATCTTCTCAAAATTCGAGT  420
      P   L   I   S   S   M   A   Q   T   L   T   L   R   S   S   S   Q   N   S   S

421  GACAAGCCTGTAGCCCACGTCGTAGCAAACCACCAAGTGGAGGAGCAGCTGGAGTGGCTG  480
      D   K   P   V   A   H   V   V   A   N   H   Q   V   E   E   Q   L   E   W   L

481  AGCCAGCGCGCCAACGCCCTCCTGGCCAACGGCATGGATCTCAAAGACAACCAACTAGTG  540
      S   Q   R   A   N   A   L   L   A   N   G   M   D   L   K   D   N   Q   L   V

541  GTGCCAGCCGATGGGTTGTACCTTGTCTACTCCCAGGTTCTCTTCAAGGGACAAGGCTGC  600
      V   P   A   D   G   L   Y   L   V   Y   S   Q   V   L   F   K   G   Q   G   C

601  CCCGACTACGTGCTCCTCACCCACACCGTCAGCCGATTTGCTATCTCATACCAGGAGAAA  660
      P   D   Y   V   L   L   T   H   T   V   S   R   F   A   I   S   Y   Q   E   K

661  GTCAACCTCCTCTCTGCCGTCAAGAGCCCCTGCCCCAAGGACACCCCTGAGGGGCTGAG  720
      V   N   L   L   S   A   V   K   S   P   C   P   K   D   T   P   E   G   A   E

721  CTCAAACCCTGGTATGAGCCCATATACCTGGGAGGAGTCTTCCAGCTGGAGAAGGGGGAC  780
      L   K   P   W   Y   E   P   I   Y   L   G   G   V   F   Q   L   E   K   G   D

781  CAACTCAGCGCTGAGGTCAATCTGCCCAAGTACTTAGACTTTGCGGAGTCCGGGCAGGTC  840
      Q   L   S   A   E   V   N   L   P   K   Y   L   D   F   A   E   S   G   Q   V

841  TACTTTGGAGTCATTGCTCTG TGA AGGGAATGGGTGTTCATCCATTCTCTACCCAGCCCC  900
      Y   F   G   V   I   A   L

901  CACTCTGACCCCTTTACTCTGACCCCTTTATTGTCTACTCCTCAGAGCCCCCAGTCTGTG  960

961  TCCTTCTAACTTAGAAAGGGGATTATGGCTCAGAGTCCAACTCTGTGCTCAGAGCTTTCA  1020

1021 ACAACTACTCAGAAACACAAGATGCTGGGACAGTGACCTGGACTGTGGGCCTCTCATGCA  1080

1081 CCACCATCAAGGACTCAAATGGGCTTTCCGAATTCACTGGAGCCTCGAATGTCCATTCCT  1140

1141 GAGTTCTGCAAAGGGAGAGTGGTCAGGTTGCCTCTGTCTCAGAATGAGGCTGGATAAGAT  1200

1201 CTCAGGCCTTCCTACCTTCAGACCTTTCCAGACTCTTCCCTGAGGTGCAATGCACAGCCT  1260

1261 TCCTCACAGAGCCAGCCCCCCTCTATTTATATTTGCACTTATTATTTATTATTTATTTAT  1320

1321 TATTTATTTATTTGCTTATGAATGTATTTATTTGGAAGGCCGGGGTGTCCTGGAGGACCC  1380

1381 AGTGTGGGAAGCTGTCTTCAGACAGACATGTTTTCTGTGAAAACGGAGCTGAGCTGTCCC  1440

1441 CACCTGGCCTCTCTACCTTGTTGCCTCCTCTTTTGCTTATGTTTAAAACAAAATATTTAT  1500

1501 CTAACCCAATTGTCTTAATAACGCTGATTTGGTGACCAGGCTGTCGCTACATCACTGAAC  1560

1561 CTCTGCTCCCCACGGGAGCCGTGACTGTAATTGCCCTACAGTCAATTGAGAGAAATAAAG  1620

1621 ATCGCTTAAAATAAAAAACCCCCC                                      1644
```

FIG. 9A

NUCLEOTIDE SEQUENCE OF HUMAN TNF cDNA

```
GGGGGGGGGAGGACCAGCTAAGAGGGAGAGAAGCAACTACAGACCCCCCCTGAAAACAAC    60
CCTCAGACGCCACATCCCCTGACAAGCTGCCAGGCAGGTTCTCTTCCTCTCACATACTGA   120
CCCACGGCTCCACCCTCTCTCCCCTGGAAAGGACACC[ATG]AGCACTGAAAGCATGATCCG   180
                                       MetSerThrGluSerMetIleArg
GGACGTGGAGCTGGCCGAGGAGGCGCTCCCCAAGAAGACAGGGGGGCCCCAGGGCTCCAG   240
AspValGluLeuAlaGluGluAlaLeuProLysLysThrGlyGlyProGlnGlySerArg
GCGGTGCTTGTTCCTCAGCCTCTTCTCCTTCCTGATCGTGGCAGGCGCCACCACGCTCTT   300
ArgCysLeuPheLeuSerLeuPheSerPheLeuIleValAlaGlyAlaThrThrLeuPhe
CTGCCTGCTGCACTTTGGAGTGATCGGCCCCCAGAGGGAAGAGTTCCCCAGGGACCTCTC   360
CysLeuLeuHisPheGlyValIleGlyProGlnArgGluGluPheProArgAspLeuSer
TCTAATCAGCCCTCTGGCCCAGGCAGTCAGATCATCTTCTCGAACCCCGAGTGACAAGCC   420
LeuIleSerProLeuAlaGlnAlaValArgSerSerArgThrProSerAspLysPro
TGTAGCCCATGTTGTAGCAAACCCTCAAGCTGAGGGGCAGCTCCAGTGGCTGAACCGCCG   480
ValAlaHisValValAlaAsnProGlnAlaGluGlyGlnLeuGlnTrpLeuAsnArgArg
GGCCAATGCCCTCCTGGCCAATGGCGTGGAGCTGAGAGATAACCAGCTGGTGGTGCCATC   540
AlaAsnAlaLeuLeuAlaAsnGlyValGluLeuArgAspAsnGlnLeuValValProSer
AGAGGGCCTGTACCTCATCTACTCCCAGGTCCTCTTCAAGGGCCAAGGCTGCCCCTCCAC   600
GluGlyLeuTyrLeuIleTyrSerGlnValLeuPheLysGlyGlnGlyCysProSerThr
CCATGTGCTCCTCACCCACACCATCAGCCGCATCGCCGTCTCCTACCAGACCAAGGTCAA   660
HisValLeuLeuThrHisThrIleSerArgIleAlaValSerTyrGlnThrLysValAsn
CCTCCTCTCTGCCATCAAGAGCCCCTGCCAGAGGGAGACCCCAGAGGGGGCTGAGGCCAA   720
LeuLeuSerAlaIleLysSerProCysGlnArgGluThrProGluGlyAlaGluAlaLys
GCCCTGGTATGAGCCCATCTATCTGGGAGGGGTCTTCCAGCTGGAGAAGGGTGACCGACT   780
ProTrpTyrGluProIleTyrLeuGlyGlyValPheGlnLeuGluLysGlyAspArgLeu
CAGCGCTGAGATCAATCGGCCCGACTATCTCGACTTTGCCGAGTCTGGGCAGGTCTACTT   840
SerAlaGluIleAsnArgProAspTyrLeuAspPheAlaGluSerGlyGlnValTyrPhe
TGGGATCATTGCCCTG[TGA]GGAGGACGAACATCCAACCTTCCCAAACGCCTCCCCTGCCC   900
GlyIleIleAlaLeuEnd
CAATCCCTTTATTACCCCCTCCTTCAGACACCCTCAACCTCTTCTGGCTCAAAAGAGAA   960
TTGGGGGCTTAGGGTCGGAACCCAAGCTTAGAACTTTAAGCAACAAGACCACCACTTCGA  1020
```

FIG. 9B

```
AACCTGGGATTCAGGAATGTGTGGCCTGCACAGTGAAGTGCTGGCAACCACTAAGAATTC   1080
AAACTGGGGCCTCCAGAACTCACTGGGGCCTACAGCTTTGATCCCTGACATCTGGAATCT   1140
GGAGACCAGGGAGCCTTTGGTTCTGGCCAGAATGCTGCAGGACTTGAGAAGACCTCACCT   1200
AGAAATTGACACAAGTGGACCTTAGGCCTTCCTCTCTCCAGATGTTTCCAGACTTCCTTG   1260
AGACACGGAGCCCAGCCCTCCCCATGGAGCCAGCTCCCTCTATTTATGTTTGCACTTGTG   1320
ATTATTTATTATTTATTTATTATTTATTTATTTACAGATGAATGTATTTATTTGGGAGAC   1380
CGGGGTATCCTGGGGGACCCAATGTAGGAGCTGCCTTGGCTCAGACATGTTTTCCGTGAA   1440
AACGGAGCTGAACAATAGGCTGTTCCCATGTAGCCCCCTGGCCTCTGTGCCTTCTTTTGA   1500
TTATGTTTTTTAAAATATTTATCTGATTAAGTTGTCTAAACAATGCTGATTTGGTGACCA   1560
ACTGTCACTCATTGCTGAGCCTCTGCTCCCCAGGGGACCCCCCCCC                 1606
```

FIG. 10

PURIFICATION SCHEME OF HUMAN TNF

| | volume mL. | TNF activity U·mL⁻¹ | TNF activity total U. | protein mg·mL⁻¹ | protein total mg. | specific activity U·mg⁻¹ | purification factor | recovery TNF activity % |
|---|---|---|---|---|---|---|---|---|
| U-937 MEDIUM | 65,000 | $3.0 \times 10^3$ | $2.0 \times 10^8$ | 0.11 | 7,150 | $2.7 \times 10^4$ | 1 | 100 |
| PELLICON CONCENTRATION | 810 | $6.0 \times 10^4$ | $4.9 \times 10^7$ | 0.88 | 713 | $6.8 \times 10^4$ | 2.5 | 24.5 |
| 1. MONO-Q POOL | 195 | $3.0 \times 10^6$ | $5.9 \times 10^7$ | 2.80 | 55 | $1.1 \times 10^6$ | 40.7 | 29.5 |
| 2. MONO Q POOL | 4.0 | $1.1 \times 10^7$ | $4.4 \times 10^7$ | 4.85 | 19.4 | $2.3 \times 10^6$ | 85.2 | 22.0 |
| TSK-G 2000 SWG POOL | 10.0 | $3.4 \times 10^6$ | $3.4 \times 10^7$ | 0.31 | 3.1 | $1.1 \times 10^7$ | 407 | 17.0 |

FIG.11

N-TERMINUS HUMAN TNF

```
                                    Ser         Pro             15
 1                                  10                          
Val - Arg - Ser - Ser - Arg - Thr - Pro -(Glu)- Asp - Lys -(Lys)- Val - Ala -(Arg)
                                                                         (Pro)
                                                                         (Asp)
```

(His) -Val -(Val) - (Ala)-

FIG. 12

Synthetic linker                              AvaI-EcoRI 669 b.p. fragment

```
       1    2    3    4    5    6    7    8    9    10   11
      Val  Arg  Ser  Ser  Ser  Arg  Thr  Pro  Ser  Asp  Lys
5'    GTA  CGT  TCT  TCC  TCT  CGT  ACC  CCGACT  GAC  AAG
3'    CAT  GCA  AGA  AGG  AGA  GCA  TGG  GGCT    CA   CTG  TTC
```

1) T4 DNA ligase
2) DNA polymerase/4 d NTPs (Klenow)

1) T4 DNA ligase
2) transformation/screening w/synthetic linker (7)

pP_L-T7-TNF-copL
≈ 4300 bp (labels: EcoRI, AvaI, PvuII, PvuII, EcoRI, AvaI, PvuII, AvaI, ori, copI, β lactamase, PstI, P_L, T, mature TNF, EcoRI)

pP_L-T7 (cop⁻)

(labels: Promoter (P_L), T7rbs, Gene, EcoRI, PstI, β lac, P_L, cop⁻, P_R, ori, SalI, AvaI)

1) SalI digest
2) S1 nuclease

153 - pL T4 hTNF CA3 (13)
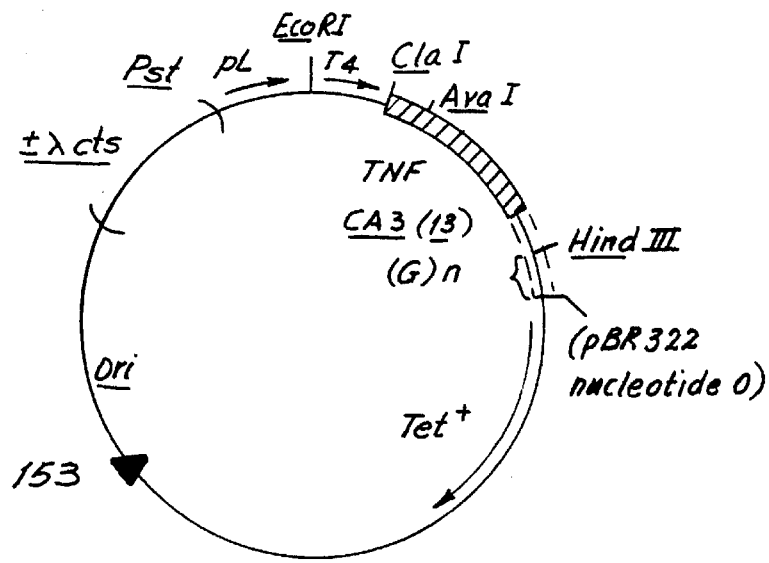
FIG.14
FIG.15
153 - T4 hTNF CA5-T4 ter
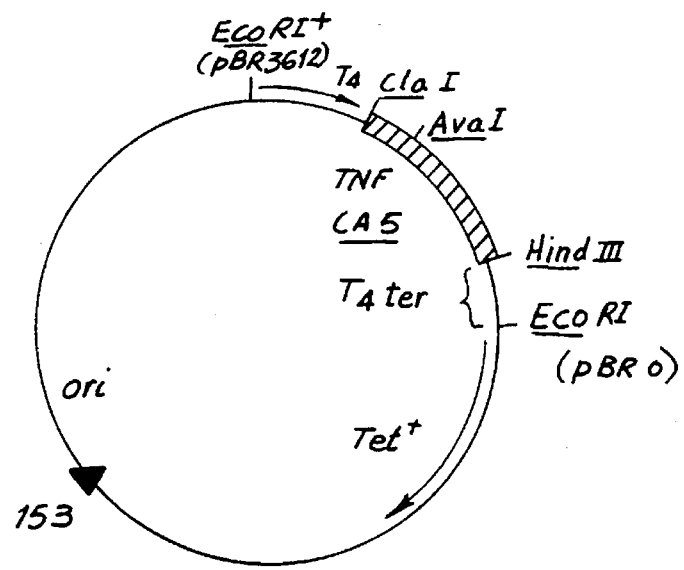

FIG. 17

```
           10                30                50
      <----------T4 SEQUENCE I------------------------------
  1   AATTCGATGGTAAAGTATTTCAACTCAGGTTGGATACCTCTCGAAGACCCAGAGTATTGC   60
      TTAAGCTACCATTTCATAAAGTTGAGTCCAACCTATGGAGAGCTTCTGGGTCTCATAACG 70                90               110
      -----------------------------------------------------------
 61   GAATTATGCCAGCTATGAGGTAAAGTGTCATAGCACCAACTGTTAATTAAATTAAATTAA  120
      CTTAATACGGTCGATACTCCATTTCACAGTATCGTGGTTGACAATTAATTTAATTTAATT 130               150               170
      -------->< ----syn. linker"CA5"---------->
121   AAAGGAAATCGATACTAAAATGGTCAGATCATCTTCTCGAACCCCGAGTGACAAGCCTGT  180
      TTTCCTTTAGCTATGATTTTACCAGTCTAGTAGAAGAGCTTGGGGCTCACTGTTCGGACA
                             MetValArgSerSerSerArgThrProSerAspLysProVa
                       <-------------TNF PROTEIN-------

190               210               230
181   AGCCCATGTTGTAGCAAACCCTCAAGCTGAGGGGCAGCTCCAGTGGCTGAACCGCCGGGC  240
      TCGGGTACAACATCGTTTGGGAGTTCGACTCCCCGTCGAGGTCACCGACTTGGCGGCCCG
      lAlaHisValValAlaAsnProGlnAlaGluGlyGlnLeuGlnTrpLeuAsnArgArgAl 250               270               290
241   CAATGCCCTCCTGGCCAATGGCGTGGAGCTGAGAGATAACCAGCTGGTGGTGCCATCAGA  300
      GTTACGGGAGGACCGGTTACCGCACCTCGACTCTCTATTGGTCGACCACCACGGTAGTCT
      aAsnAlaLeuLeuAlaAsnGlyValGluLeuArgAspAsnGlnLeuValValProSerGl 310               330               350
301   GGGCCTGTACCTCATCTACTCCCAGGTCCTCTTCAAGGGCCAAGGCTGCCCCTCCACCCA  360
      CCCGGACATGGAGTAGATGAGGGTCCAGGAGAAGTTCCCGGTTCCGACGGGGAGGTGGGT
      uGlyLeuTyrLeuIleTyrSerGlnValLeuPheLysGlyGlnGlyCysProSerThrHi 370               390               410
361   TGTGCTCCTCACCCACACCATCAGCCGCATCGCCGTCTCCTACCAGACCAAGGTCAACCT  420
      ACACGAGGAGTGGGTGTGGTAGTCGGCGTAGCGGCAGAGGATGGTCTGGTTCCAGTTGGA
      sValLeuLeuThrHisThrIleSerArgIleAlaValSerTyrGlnThrLysValAsnLe 430               450               470
421   CCTCTCTGCCATCAAGAGCCCCTGCCAGAGGGAGACCCCAGAGGGGGCTGAGGCCAAGCC  480
      GGAGAGACGGTAGTTCTCGGGGACGGTCTCCCTCTGGGGTCTCCCCCGACTCCGGTTCGG
      uLeuSerAlaIleLysSerProCysGlnArgGluThrProGluGlyAlaGluAlaLysPr 490               510               530
481   CTGGTATGAGCCCATCTATCTGGGAGGGGTCTTCCAGCTGGAGAAGGGTGACCGACTCAG  540
      GACCATACTCGGGTAGATAGACCCTCCCCAGAAGGTCGACCTCTTCCCACTGGCTGAGTC
      oTrpTyrGluProIleTyrLeuGlyGlyValPheGlnLeuGluLysGlyAspArgLeuSe 550               570               590
541   CGCTGAGATCAATCGGCCCGACTATCTCGACTTTGCCGAGTCTGGGCAGGTCTACTTTGG  600
      GCGACTCTAGTTAGCCGGGCTGATAGAGCTGAAACGGCTCAGACCCGTCCAGATGAAACC
      rAlaGluIleAsnArgProAspTyrLeuAspPheAlaGluSerGlyGlnValTyrPheGl 610               630               650
                         <-------syn. T4 gene 32 terminator-->
601   GATCATTGCCCTGTGAGTCGAAGCTTGGGGACCCTAGAGGTCCCCTTTTTTATTTTGAAT  660
      CTAGTAACGGGACACTCAGCTTCGAACCCCTGGGATCTCCAGGGGAAAAAATAAAACTTA
      yIleIleAlaLeuEnd

```
            10                 30                 50
         <--------------------pL promoter------------------------
  1   CTGCAGCCCACGATGCGTCCGGCGTAGAGGATCTCTCACCTACCAAACAATGCCCCCCTG   60
      GACGTCGGGTGCTACGCAGGCCGCATCTCCTAGAGAGTGGATGGTTTGTTACGGGGGGAC 70                 90                110
      ------------------------------------------------------------
 61   CAAAAAATAAATTCATATAAAAAACATACAGATAACCATCTGCGGTGATAAATTATCTCT  120
      GTTTTTTATTTAAGTATATTTTTTGTATGTCTATTGGTAGACGCCACTATTTAATAGAGA 130                150                170
      ------------------------------------------------------------
121   GGCGGTGTTGACATAAATACCACTGGCGGTGATACTGAGCACATCAGCAGGACGCACTGA  180
      CCGCCACAACTGTATTTATGGTGACCGCCACTATGACTCGTGTAGTCGTCCTGCGTGACT 190                210                230
      ------------------------------------------------------------
181   CCACCATGAAGGTGACGCTCTTAAAATTAAGCCCTGAAGAAGGGCAGCATTCAAAGCAGA  240
      GGTGGTACTTCCACTGCGAGAATTTTAATTCGGGACTTCTTCCCGTCGTAAGTTTCGTCT 250                270                290
      ---------------------------------------->  <-----T4sequence----
241   AGGCTTTGGGGTGTGTGATACGAAACGAAGCATTGGAATTCGATGGTAAAGTATTTCAAC  300
      TCCGAAACCCCACACACTATGCTTTGCTTCGTAACCTTAAGCTACCATTTCATAAAGTTG 310                330                350
      ------------------------------------------------------------
301   TCAGGTTGGATACCTCTCGAAGACCCAGAGTATTGCGAATTATGCCAGCTATGAGGTAAA  360
      AGTCCAACCTATGGAGAGCTTCTGGGTCTCATAACGCTTAATACGGTCGATACTCCATTT 370                390                410
      ---------------------------------------->< ---syn. linker
361   GTGTCATAGCACCAACTGTTAATTAAATTAAATTAAAAAGGAAATCGATACTATGGTCAG  420
      CACAGTATCGTGGTTGACAATTAATTTAATTTAATTTTTCCTTTAGCTATGATACCAGTC
                                                        MetValAr
                                                        <-------

"CA3"---------->    430                450                470
421   GTCTTCCTCTCGAACCCCGAGTGACAAGCCTGTAGCCCATGTTGTAGCAAACCCTCAAGC  480
      CAGAAGGAGAGCTTGGGGCTCACTGTTCGGACATCGGGTACAACATCGTTTGGGAGTTCG
      gSerSerSerArgThrProSerAspLysProValAlaHisValValAlaAsnProGlnAl
      ----TNF protein------
           490                510                530
481   TGAGGGGCAGCTCCAGTGGCTGAACCGCCGGGCCAATGCCCTCCTGGCCAATGGCGTGGA  540
      ACTCCCCGTCGAGGTCACCGACTTGGCGGCCCGGTTACGGGAGGACCGGTTACCGCACCT
      aGluGlyGlnLeuGlnTrpLeuAsnArgArgAlaAsnAlaLeuLeuAlaAsnGlyValGl 550                570                590
541   GCTGAGAGATAACCAGCTGGTGGTGCCATCAGAGGGCCTGTACCTCATCTACTCCCAGGT  600
      CGACTCTCTATTGGTCGACCACCACGGTAGTCTCCCGGACATGGAGTAGATGAGGGTCCA
      uLeuArgAspAsnGlnLeuValValProSerGluGlyLeuTyrLeuIleTyrSerGlnVa 610                630                650
601   CCTCTTCAAGGGCCAAGGCTGCCCCTCCACCCATGTGCTCCTCACCCACACCATCAGCCG  660
      GGAGAAGTTCCCGGTTCCGACGGGGAGGTGGGTACACGAGGAGTGGGTGTGGTAGTCGGC
      lLeuPheLysGlyGlnGlyCysProSerThrHisValLeuLeuThrHisThrIleSerAr 670                690                710
661   CATCGCCGTCTCCTACCAGACCAAGGTCAACCTCCTCTCTGCCATCAAGAGCCCCTGCCA  720
      GTAGCGGCAGAGGATGGTCTGGTTCCAGTTGGAGGAGAGACGGTAGTTCTCGGGGACGGT
      gIleAlaValSerTyrGlnThrLysValAsnLeuLeuSerAlaIleLysSerProCysGl
```

FIG. 18B

```
            730                 750                 770
721  GAGGGAGACCCCAGAGGGGGCTGAGGCCAAGCCCTGGTATGAGCCCATCTATCTGGGAGG  780
     CTCCCTCTGGGGTCTCCCCCGACTCCGGTTCGGGACCATACTCGGGTAGATAGACCCTCC
     nArgGluThrProGluGlyAlaGluAlaLysProTrpTyrGluProIleTyrLeuGlyGl 790                 810                 830
781  GGTCTTCCAGCTGGAGAAGGGTGACCGACTCAGCGCTGAGATCAATCGGCCCGACTATCT  840
     CCAGAAGGTCGACCTCTTCCCACTGGCTGAGTCGCGACTCTAGTTAGCCGGGCTGATAGA
     yValPheGlnLeuGluLysGlyAspArgLeuSerAlaGluIleAsnArgProAspTyrLe 850                 870                 890   ⟵----
841  CGACTTTGCCGAGTCTGGGCAGGTCTACTTTGGGATCATTGCCCTGTGAGTCGAAGCTTG  900
     GCTGAAACGGCTCAGACCCGTCCAGATGAAACCCTAGTAACGGGACACTCAGCTTCGAAC
     uAspPheAlaGluSerGlyGlnValTyrPheGlyIleIleAlaLeuEnd 910                 930
     --syn.  T4 terminator--------->
901  GGGACCCTAGAGGTCCCCTTTTTTATTTTGAATTC   935
     CCCTGGGATCTCCAGGGGAAAAAATAAAACTTAAG
```

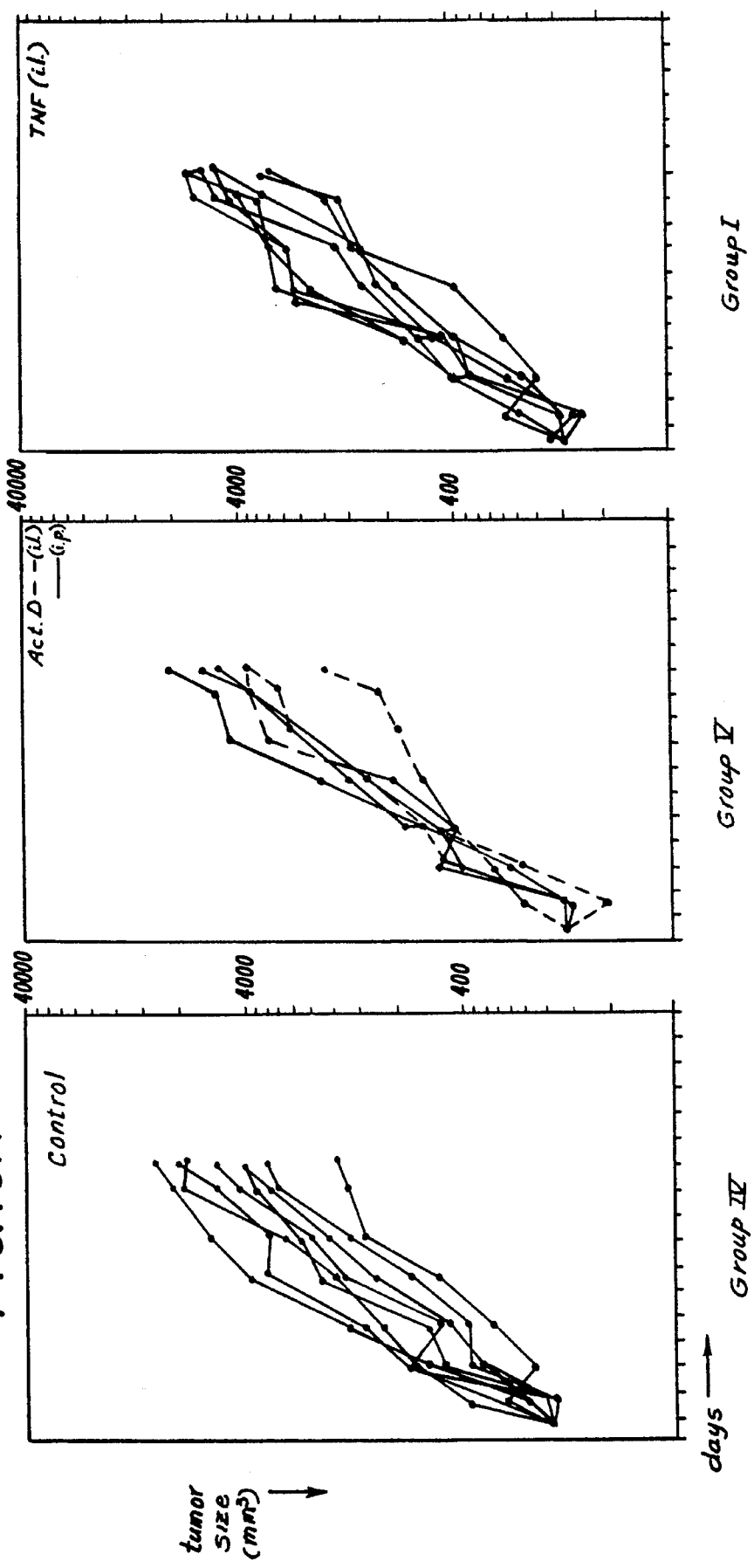

PROCESSES FOR PRODUCING TUMOR NECROSIS FACTOR

TECHNICAL FIELD OF INVENTION

This is a continuation-in-part of application Ser. No. 684,595, filed Dec. 21, 1984, now abandoned, entitled Processes For Purifying Tumor Necrosis Factors And For Producing DNA Sequences Coding For Tumor Necrosis Factor-Like Compounds And Tumor Necrosis Factors and Ser. No. 785,847, filed Oct. 9, 1985, now abandoned, entitled Expression System For Overproduction Of Desired Proteins.

This invention relates to tumor necrosis factors (TNF) and to compounds having enhanced cytotoxic or cytostatic activity for transformed cells. More particularly, the invention relates to a process for producing tumor necrosis factor-like polypeptides. Most particularly, this invention relates to the production of TNF-like polypeptides by hosts transformed with recombinant DNA molecules comprising DNA sequences encoding those polypeptides, to the TNF-like polypeptides produced, and to methods of treatment and compositions characterized by those TNF-like polypeptides. These methods and agents are useful in a variety of antitumor, anticancer and antimalarial applications and therapies. They are also useful for such anticancer and antitumor therapies in combination with interferons, e.g., IFN-$\alpha$, IFN-$\beta$ and IFN-$\gamma$, together with chemotherapy, and in combination with antibiotics, such as actinomycin D.

BACKGROUND ART

TNF is produced by macrophages and mononuclear phagocytes. It is cytotoxic or cytostatic for a broad range of animal and human cancer cells in vitro and induces hemorrhagic necrosis in certain animal tumors and heterotransplanted human tumors in vivo [K. Haranaka and N. Satomi, "Note: Cytotoxic Activity of Tumor Necrosis Factor (TNF) on Human Cancer Cells in vitro", *Japan J. Exp. Med.*, 51, pp. 191–94 (1981); L. Old, "Cancer Immunology: The Search for Specificity— G.H.A. Clowes Memorial Lecture", Cancer Research, 41, pp. 361–75 (1981)].

Compounds displaying TNF activity have been obtained from sera of mice and rabbits that have been infected with Bacillus-Calmette-Guerin (BCG) or Corynebacterium and treated with lipopoly-saccharide (LPS) of *Escherichia coli* [E. A. Carswell et al., "An Endotoxin-Induced Serum Factor That Causes Necrosis Of Tumors", *Proc. Natl. Acad. Sci. USA*, 72, pp. 3666–70 (1975)]. They have also been derived from the incubation media of macrophage-enriched peritoneal exudate cells of mice infected with BCG, as well as from macrophage-like tumor cells (PU5-1.8) and peritoneal macrophages of pretreated mice, which have been propagated in vitro with macrophage growth factor and stimulated with LPS [D. Mannel, R. Moore and S. Mergenhagen, "Macrophages as a Source of Tumoricidal Activity (Tumor Necrotizing Factor)", Infect. Immun., 30, pp. 523-30 (1980)].

Furthermore, when human monocytes, which are macrophage precursors, are isolated, for example, from the blood of healthy human donors, and are stimulated with lymphokines and/or LPS, they produce chemical agents having cytotoxic or cytostatic effects on murine target cells and human transformed cells [N. Matthews, "Production of an Anti-tumour Cytotoxin by Human Monocytes: Comparison of Endotoxin, Interferons and Other Agents as Inducers", *Br. J. Cancer*, 45, pp. 615–17 (1982); J. Hammerstrøm, "Soluble Cytostatic Factor(s) Released from Human Monocytes: I. Production and Effect on Normal and Transformed Human Target Cells", *Scand. J. Immunol.*, 15, pp. 311–18 (1982)]. Accordingly, as TNF is produced (after appropriate treatment) by monocyte-derived cells, the substance is sometimes referred to as "monocyte cytotoxin" [D. S. Stone-Wolf et al., "Interrelationships Of Human Interferon-Gamma With Lymphotoxin And Human Cytotoxin", *J. Exp. Med.*, 159, pp. 820–43 (1984)].

A fraction of the $\alpha_1$-$\alpha_2$ globulins from the serum of normal humans has also been shown to be toxic to tumors in mice and to inhibit the growth in vitro of human colon cancer, melanoma and neuroblastoma cell lines [U.S. Pat. No. 4,309,418; S. Green et al., Cancer Letters, 6, pp. 235–40 (1979); *J. Cell. Biol.*, 79, p. 67 (1978)].

However, at present, animal and human TNFs have been produced only in extremely small quantities. The processes for the production of animal TNFs entail either sacrificing large numbers of pretreated mice or rabbits and purifying their sera to recover the TNFs or collecting their macrophages, stimulating the cells in vitro and recovering and purifying the produced TNFs from the supernatant. The collection of cells from human donors for in vitro incubation to produce TNFs and the purification of the $\alpha$-globulin fraction of serum from human donors to recover the antitumor agents are, likewise, not useful on a large scale. Furthermore, all of these procedures are time-consuming, expensive, and provide very low yields of TNF.

DISCLOSURE OF THE INVENTION

The present invention solves the problems referred to above by providing a process for producing commercially significant quantities of TNF-like compounds and TNFs of sufficient purity for use in anticancer and antitumor compositions, methods and therapies. Accordingly, this invention affords the production of TNFs or TNF-like polypeptides, in amounts and by methods hitherto not available, for use in anticancer and antitumor compositions and methods.

Other objects of this invention include the location and identification of DNA sequences that code for TNF-like polypeptides, the transformation of a variety of hosts with these DNA sequences and the production of TNF or TNF-like polepeptides in those transformed hosts. Among the TNF-like polypeptides and TNFs produced according to this invention are mammalian TNFs, such as rabbit, mouse and human TNFs.

As will be appreciated from the disclosure to follow, another object of this invention is the purification of TNF from natural sources. Once the native TNF is purified, its amino acid sequence can be determined and DNA probes be synthesized based on that amino acid sequence. These DNA probes which can then be employed in screening collections of DNA sequences from a variety of natural and synthetic sources to select TNF-related DNA sequences for the subsequent expression of TNFs and TNF-like compounds in accordance with the processes of this invention.

This purified TNF is also useful in another aspect of this invention, the enhancement of growth inhibition or killing of tumor cells through the use of combinations of natural or recombinant TNFs and antibiotics such as actinomycin D. According to this method, tumor bearing mammals are treated with pharmaceutically effective amounts of TNF and actinomycin D to enhance the effect of TNFs on tumor cells.

As will be appreciated from the disclosure to follow, the DNA sequences and recombinant DNA molecules of the invention are capable of directing the production, in an appropriate host, of TNFs or TNF-like polypeptides. Replication of these DNA sequences and recombinant DNA molecules in appropriate hosts also permits the production in large quantities of genes coding for these polypeptides. The molecular structure and properties of these polypeptides and genes may thus be readily determined. The polypeptides and genes are useful, either as produced in the host or after appropriate derivatization or modification, in compositions and methods for detecting and improving the production of these products themselves and for use in anticancer, antitumor and antimalarial compositions and methods.

It will be appreciated from the foregoing that a basic aspect of this invention is the provision of a DNA sequence, which is characterized in that it codes for TNF or a TNF-like polypeptide, or at least allows the selection of such DNA sequences, from a collection of DNA sequences. These DNA sequences are selected from the group consisting of:

(a) the DNA inserts of p-mTNF-3;

(b) the DNA inserts of p-hTNF-1;

(c) DNA sequences that hybridize to one or both of DNA inserts (a) and (b) and which code on expression for a TNF-like polypeptide; and (d) DNA sequences that code on expression for a polypeptide coded on expression by any of the foregoing DNA inserts and sequences.

The DNA sequences of this invention are further characterized in that they permit the production of TNF or TNF-like polypeptides in appropriate hosts transformed with them.

BRIEF DESCRIPTION OF THE DRAWINGS

FIGS. 4 and 5 depict the amino acid sequence of two portions— TNF Fragment 3 and 4 — of rabbit TNF purified by the processes of this invention. FIGS. 4 and 5 also depict various nucleotide sequences that code for those amino acid sequence portions and the nucleotide sequences of various DNA probes synthesized from those DNA sequences.

FIG. 6 also depicts the partial restriction map of those three clones. Finally, FIG. 6 depicts the two internal RsaI and PvuII restriction fragments of p-mTNF-1 that we used for subsequent hybridization screening of various DNA libraries.

FIG. 7 depicts the nucleotide sequence of a mouse TNF cDNA and the amino acid sequence derived from it.

FIG. 8 also depicts the partial restriction map of that clone.

FIGS. 9A and 9B depict the nucleotide sequence of the cDNA insert of p-hTNF-1 and the amino acid sequence derived from it.

FIG. 10 depicts in schematic outline one embodiment of a process according to this invention for purifying TNF-like polypeptides from the medium of induced U-937 human cells.

FIG. 11 depicts the N-terminal amino acid sequence determined by amino acid sequencing of a sample of human TNF purified by the processes of this invention.

FIG. 12 depicts in schematic outline one embodiment of a process for constructing a recombinant expression vector characterized by a DNA sequence coding on expression for human TNF.

FIG. 14 depicts recombinant expression vector 153-pL-T4-hTNF-CA3 (13) characterized by a DNA sequence coding on expression for human TNF.

FIG. 15 depicts recombinant expression vector 153-T4-hTNF-CA5-T4ter characterized by a DNA sequence coding on expression for human TNF.

FIG. 17 depicts the DNA sequence and derived amino sequence of plasmid 153-T4-hTNF-CA5-T4-ter from the DRAI AATTC EcoRI site to the EcoRI site located at the end of the T4-ter hTNF gene.

FIGS. 18A and 18B depict the DNA sequence and derived amino acid sequence of plasmid 153-pL-T4-CA3-cts-T4-ter from the PstI site to the Eco RI site.

FIGS. 19A, 19B, 19C, 20A and 20B depict a graphic representation of the effect on tumor growth of the combination of actinomycin D and TNF.

DETAILED DESCRIPTION OF THE INVENTION

Figure 1A:
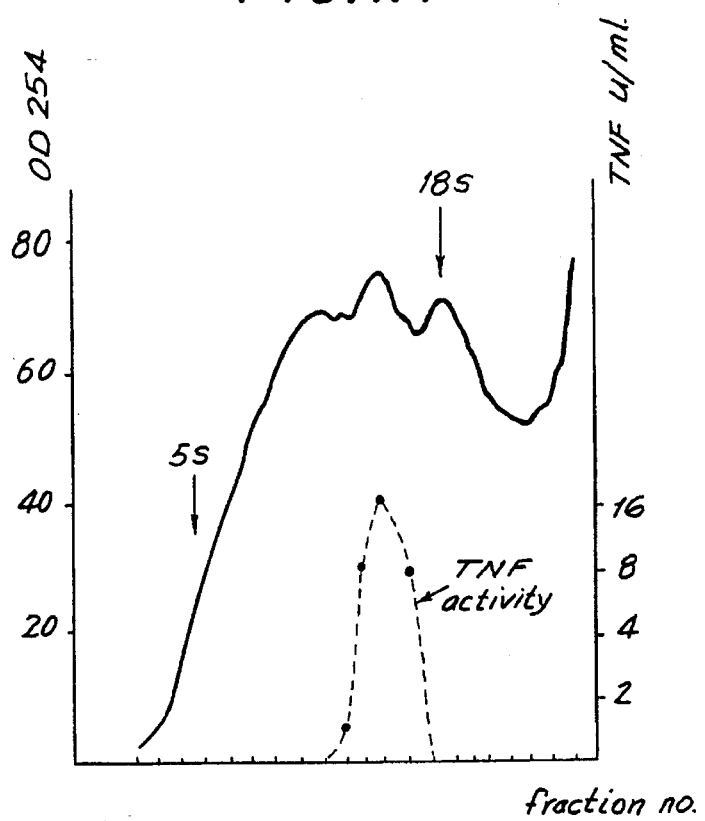
FIGS. 1A and 1B depict the OD-profile of two representative sucrose gradients of human (A) and mouse (B) mRNA preparations. On the first gradient, we loaded 750 μg of human poly $A^+$mRNA. On the second gradient we loaded 200 μg of mouse poly $A^+$RNA. We assayed the biological activity of each fraction in *Xenopus laevis* oocytes.

In order that the invention herein described may be fully understood, the following detailed description is set forth.

In the description, the following terms are employed:

Nucleotide— A monomeric unit of DNA or RNA consisting of a sugar moiety (pentose), a phosphate, and a nitrogenous heterocyclic base. The base is linked to the sugar moiety via the glycosidic carbon (1' carbon of the pentose). That combination of a base and a sugar is called a nucleoside. Each nucleotide is characterized by its base. The four DNA bases are adenine ("A"), guanine ("G"), cytosine ("C") and thymine ("T"). The four RNA bases are A, G, C and uracil ("U").

DNA Sequence— A linear array of nucleotides connected one to the other by phosphodiester bonds between the 3' and 5' carbons of adjacent pentoses.

Codon— A DNA sequence of three nucleotides (a triplet) which encodes through mRNA an amino acid, a translation start signal or a translation termination signal.

Gene— A DNA sequence which encodes through its template or messenger RNA ("mRNA") a sequence of amino acids characteristic of a specific polypeptide.

Transcription— The process of producing mRNA from a gene.

Translation— The process of producing a polypeptide from mRNA.

Expression— The process undergone by a DNA sequence or gene to produce a polypeptide. It is a combination of transcription and translation.

Plasmid— A non-chromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. For example, a plasmid carrying the gene for tetracycline resistance ($Tet^R$) transforms a cell previously sensitive to tetracycline into one which is resistant to it. A cell transformed by a plasmid is called a "transformant".

Phage or Bacteriophage— Bacterial virus many of which consist of DNA sequences encapsidated in a protein envelope or coat ("capsid").

Cloning Vehicle— A plasmid, phage DNA or other DNA sequence which is able to replicate in a host cell, which is characterized by one or a small number of endonuclease recognition sites at which such DNA sequence may be cut in a determinable fashion without attendant loss of an essential biological function of the DNA, e.g., replication, production of coat proteins or loss of promoter or binding sites, and which contains a marker suitable for use in the identification of transformed cells, e.g., tetracycline resistance or ampicillin resistance. A cloning vehicle is often called a vector.

Cloning— The process of obtaining a population of organisms or DNA sequences derived from one such organism or sequence by asexual reproduction.

Recombinant DNA Molecule or Hybrid DNA— A molecule consisting of segments of DNA from different genomes which have been joined end-to-end and have the capacity to infect some host cell and be maintained therein.

Expression Control Sequence— A sequence of nucleotides that controls and regulates expression of genes when operatively linked to those genes. They include the lac system, the trp system, the tac system, the trc system, major operator and promoter regions of phage λ, the control region of fd coat protein, the early and late promoters of SV40, promoters derived from polyoma, adenovirus and simian virus, the promoter for 3-phosphoglycerate kinase or other glycolytic enzymes, the promoters of yeast acid phosphotase, e.g., Pho 5, the promoters of the yeast α-mating factors, and other sequences known to control the expression of genes of prokaryotic or eukaryotic cells and their viruses, or combinations thereof.

Lymphokine— A soluble, humoral mediator that is released by primed lymphocytes when they are contacted by specific antigens. Lymphokines include, for example, interferons and macrophage activation factors.

TNF (Tumor necrosis factor)— TNF is a growth inhibitory or cytotoxic lymphokine. As used in this application, "TNF" includes all proteins, polypeptides, and peptides which are natural or recombinant TNFs, or derivatives thereof, and which are characterized by the tumoricidal activity or the inhibition of tumor growth of these TNFs. They include TNF-like compounds from a variety of sources, such as natural TNFs, recombinant TNFs, and synthetic or semi-synthetic TNFs. They also include polypeptides of the TNF-type coded for by DNA sequences, including single or multiple base substitutions, deletions, insertions and inversions to any DNA sequence coding for TNF.

TNF-like polypeptide— A polypeptide displaying a biological activity of TNF. It includes mammalian TNFs, such as rabbit, mouse and human TNFs, and TNF-like polypeptides.

Tumor— As used in this application, the term "tumor" encompasses any undesirable proliferation of cells. Such proliferation includes malignant and non-malignant, solid or fluid tumors, carcinomas, myelomas, sarcomas, leukemias, lymphomas, and other cancerous, neoplastic, or tumorigenic diseases.

Actinomycin— Actinomycins are a class of antibiotics which are believed to impede DNA transcription by blocking the function of RNA polymerases. As used in this application, "actinomycin" includes related members of the family of antibiotics generally known as actinomycin, as well as their derivatives. The term includes, for example, actinomycin D.

LPS— An endotoxin consisting of lipopoly-saccharide derived from the cell walls of *E. coli.* (0.55:B5) (Difco, Detroit, Mich.).

BCG— Bacillus Calmette-Guerin (Pasteur Institut, Brussels)

This invention relates to identifying at least one DNA sequence that codes for a TNF-like polypeptide and expressing that DNA in a host transformed with it. In addition, a purification process characterized by the steps of contacting a composition containing a TNF-like polypeptide with an anion exchanger, removing the components of the composition remaining unbound to the exchanger and eluting the TNF-like polypeptide from the exchanger, is encompassed herein.

In general outline, one embodiment of our process of purifying TNF-like polypeptides from natural sources comprises the steps of pooling the serum of animals, preferably rabbits, which have been specially treated to induce the production of TNF; precipitating the active components in the serum with a base, preferably by means of ammonium sulfate, e.g., to about 60% saturation; resuspending the pellet in a neutral-slightly basic buffer, preferably Tris-HCl, and fractionating the proteins using ion exchange column chromatography, preferably DEAE-Sephacel, using a salt gradient; concentrating the pooled fractions containing TNF activity, preferably on an Amicon TCF-2 apparatus; fractionating the concentrate by molecular weight on a gel filtration chromatographic column, preferably AcA34; pooling the fractions containing TNF activity and subjecting them to ion-exchange chromatography, preferably on Mono Q columns (Pharmacia), first at a slightly basic pH and then at a slightly acidic pH. It should, of course, be understood that this purification process, and particularly the use of the anion exchanger may be employed to purify TNF-like polypeptides from a wide variety of natural sources, as well as from a variety of prokaryotic and eukaryotic hosts transformed with DNA sequences coding for those polypeptides.

The amino acid sequences of the purified TNFs that result from the above-described process may then be determined. These resulting amino acid sequences may also be employed in a variety of ways in accordance with this invention. They can be used to prepare a series of DNA probes that are useful in screening various collections of natural and synthetic mammalian DNAs for the presence of DNA sequences that code for the TNF-like polypeptides and TNFs of this invention. For example, a DNA sequence derived from the amino acid sequence of a rabbit TNF may be used to screen DNA libraries for other DNA sequences coding for rabbit or other mammalian TNF-like polypeptides. Furthermore, such a DNA sequence, or more preferably rabbit or mouse DNA sequences selected by it, may also be used to screen for DNA sequences coding for human TNF-like polypeptides because of the expected homologies between rabbit, mouse, and human TNFs.

These DNA sequences are then employed in this invention to produce those TNF-like polypeptides on expression in various prokaryotic and eukaryotic hosts transformed with them. These TNF-like polypeptides may be used in anti-cancer and anti-tumor applications and therapy. In general outline, this second embodiment of the invention comprises the steps of culturing a prokaryotic or eukaryotic host transformed by a recombinant DNA molecule containing a DNA sequence encoding the desired TNF-like polypeptide, the sequence being operatively-linked to an expression control sequence in the recombinant DNA molecule. Again, because of the expected similarities between rabbit TNF, or other mammalian TNFs, and human TNF, any of them may be useful in accordance with this invention in therapy against human cancers and tumors and against malarial infections.

In addition, purified TNF, derived from natural or recombinant sources, can be used in the combinations of this invention, such as in the combination of TNF and actinomycin D. More particularly, according to the methods of this invention, they can be used in pharmaceutically effective amounts, in combination with pharmaceutically effective amounts of actinomycin D to treat tumors.

Conventional treatment of tumors include non-surgical treatments, such as chemotherapy and radiation, and surgical treatments. Typically, these treatments are characterized by various undesirable side effects. Non-surgical treatments having immuno-suppressant effects may increase the patient's susceptibility to secondary infections. Surgical treatments to excise transformed cells involve risks attendant with invasive procedures and may not effectively remove or eliminate the entire transformed cell population. Alternative methods of treatment for cancers and non-malignant tumors have involved the use of monoclonal antibodies to tumor specific antigens on the surface of transformed cells. The effectiveness of such treatments, typically involving murine monoclonal antibodies, is often limited by a variety of factors, including anti-antibody responses which impede the effectiveness of further administrations of the murine antibody [G. E. Goodman et al., "Pilot Trial of Murine Monoclonal Antibodies In Patients With Advanced Melanoma", *Journal Of Clinical Oncology*, 3, pp. 340–51 (1985)]. Other reported side effects of monoclonal antibody treatments include anaphylaxis, fever and chills.

In view of the disadvantages of such therapies, various therapies have been directed to augmenting the body's immune response to tumorigenic cells by increasing the body's level of various lymphokines. For example, TNF alone is known to inhibit the growth of or to kill tumor cells. In addition, combinations of human lymphotoxin and human gamma interferon have been reported to inhibit tumor growth [European patent application 128,009]. Combinations of TNF and human interferon have also been reported to demonstrate a greater growth inhibitory or cytotoxic effect on human tumors than the sum of their separate effects [L. Fransen et al., "Recombinant Tumor Necrosis Factor: Its Effect And Its Synergism With Interferon-γ. On A Variety Of Normal And Transformed Human And Mouse Cell Lines", *Eur. J. of Cancer and Clinical Oncology*, (in press); see also European Patent Application 131,789]. Finally, combinations of actinomycin D and TNF have been reported to demonstrate inhibition of tumor cell growth in vitro. [J. M. Ostrone and G. E. Gifford, "Stimulation Of RNA Synthesis In L-929 Cells By Rabbit Tumor Necrosis Factor (40449)", *Proc. Soc. Exp. Biol. Med.*, 160, pp. 354–58 (1978); M. R. Ruff and G. E. Gifford, "Rabbit Tumor Necrosis Factor: Mechanism Of Action", Infection and Immunity, 31, pp. 380–85 (1985)].

Referring now to the production of TNF-like polypeptides coded for on expression by the DNA sequences of this invention, we chose to select the first of our TNF-related DNA sequences using DNA probes that comprised a series of synthetic DNA fragments prepared on the basis of partial amino acid segments of rabbit TNF purified by processes of this invention. It should be understood that a variety of cloning and selection techniques might theoretically have been useful in locating and identifying the DNA sequences of this invention that encode our TNF and TNF-like polypeptides. Our selected DNA sequences were then used themselves as probes to select other rabbit and mammalian DNA sequences coding for TNF-like polypeptides and to transform appropriate eukaryotic and prokaryotic hosts for the production of the TNF-like polypeptides encoded by them. Furthermore, the DNA sequences selected by our rabbit DNA probes were also used themselves to select DNAs coding for mammalian TNFs and TNF-like polypeptides and those latter DNA sequences used to produce those polypeptides in appropriate eukaryotic and prokaryotic hosts.

The DNA sequences and recombinant DNA molecules of the present invention could have been expressed using a wide variety of host/vector combinations. For example, useful vectors may consist of segments of chromosomal, non-chromosomal and synthetic DNA sequences, such as various known derivatives of SV40 and known bacterial plasmids, e.g., plasmids from *E. coli* including colE1, pCR1, pBR322, pMB9 and their derivatives, wider host range plasmids, e.g., RP4, phage DNAs, e.g., the numerous derivatives of phage λ, e.g., NM 989, and other DNA phages, e.g., M13 and Filameneous single-stranded DNA phages, vectors useful in yeasts, such as the 2μ plasmid, vectors useful in eukaryotic cells, such as vectors useful in animal cells, such as those containing SV-40 derived DNA sequences, and vectors derived from combinations of plasmids and phage DNAs, such as plasmids which have been modified to employ phage DNA or other derivatives thereof.

Such expression vectors are also characterized by at least one expression control sequence that may be operatively linked to the TNF-DNA sequence inserted in the vector in order to control and to regulate the expression of that cloned DNA sequence. Examples of useful expression control sequences are the lac system, the trp system, the tac system, the trc system, major operator and promoter regions of phage λ, the control region of fd coat protein, the glyeolytic promoters of yeast, e.g., the promoter for 3-phosphoglycerate kinase, the promoters of yeast acid phosphatase, e.g., Pho5, the promoters of the yeast α-mating factors, and promoters derived from polyoma, adenovinus and simian virus, e.g., the early and late promoters or SV40, and other sequences known to control the expression of genes of prokaryotic or eukaryotic cells and their viruses or combinations thereof.

Among such useful expression vectors are vectors that enable the expression of the cloned TNF-related DNA sequences in eukaryotic hosts, such as animal and human cells [e.g., P. J. Southern and P. Berg, *J. Mol. Appl. Genet.*, 1, pp. 327–41 (1982); S. Subramani et al., *Mol. Cell. Biol.*, 1, pp. 854–64 (1981); R. J. Kaufmann and P. A. Sharp, "Amplification And Expression Of Sequences Cotransfected With A Modular Dihydrofolate Reductase Complementary DNA Gene", *J. Mol. Biol.*, 159, pp. 601–21 (1982); R. J. Kaufmann and P. A. Sharp, *Mol. Cell. Biol.*, 159, pp. 601–64 (1982) S. I. Scahill et al., "Expression And Characterization Of The Product Of A Human Immune Interferon DNA Gene in Chinese Hamster Ovary Cells", *Proc. Natl. Acad. Sci. U.S.A.*, 80, pp. 4654–59 (1983); G. Urlaub and L. A. Chasin, *Proc. Natl. Acad. Sci. USA*, 77, pp. 4216–20 (1980)].

We found the T4 expression control sequence alone to be particularly useful in the recombinant DNA molecules of this invention. For example, particularly effective expression of TNF-like polypeptides may be obtained by using, as part of an expression system, a plasmid comprising a DNA sequence derived from bacteriophage T4 that comprises both a promoter and a ribosome binding site. This sequence is a deletion derivative of the phage T4 protein 32 (gp 32) gene [H. M. Krisch and B. Allet, "Nucleotide Sequences Involved In Bacteriophage T4 gene 32: Translational Self-Relation", *Proc Natl. Acad. Sci.*, 79, pp. 4937–41 (1982)].

We believe that at least one reason why the fragment of the T4 DNA sequence utilized in our invention is so effective is that within said fragment there are three or four contiguous segments, each of which may function as a promoter (i.e., to initiate transcription of mRNA), in sequence and that these promoters may sequester several RNA polymerase molecules, initiating more mRNAs than would a single promoter. Finally, we have found that the mRNA initiating in the T4 DNA sequence is unusually stable in *E. coli.* [see K. Gorski et al. Cell (1985) (in press)].

In a preferred embodiment, this invention relates to recombinant DNA molecules comprising the following expression control sequences:

```
CGAT GGT AAAGT ATTT CAACT CAGGT T GGAT ACCT CT CGAAGACCCAGAG
T ATT GCGAATT AT GCCAGCT AT GAGGT AAAGT GT CAT AGCACCAACGTT A
ATT AAATT AAATT AAAAAAGGAAAT X AT G
``` wherein X is absent (in which case, the last five bases may be represented by ATATG) or X is a group of 1 to 15 bases. Preferably, X is selected from the group consisting of CGATACT, CGCGATACT, ATACTAAA, ATACT, CGCGATACTAAA and CGATACTAAA.

The expression control sequence wherein X is absent may also be represented as follows:

```
CGAT GGT AAAGT AT TT C AACT CAGGT T GGAT ACCT CT CGAAG
ACCCAGAGT AT T GCGAATT AT GCCAGCT AT GAGGT AAAGT GT CAT AGCACCA
ACGT T AATT AAATT AAATT AAAAAAGGAAAT AT G.
```

The preferred expression control sequences may also be represented as follows:

```
                CGAT GGT AAAGT ATTT C AACT CAGGT T GGAT ACCT CT CGAAG
ACCCAGAGT AT T GCGAATT AT GCCAGCT AT GAGGT AAAGT GT CAT AGCACCA
ACGT T AATT AAATT AAATT AAAAAAGGAAAT CGAT ACT AT G;
                CGAT GGT AAAGT ATTT C AACT CAGGT T GGAT ACCT CT CGAAG
ACCCAGAGT AT T GCGAATT AT GCCAGCT AT GAGGT AAAGT GT CAT AGCACCA
ACGT T AATT AAATT AAATT AAAAAAGGAAAT CGCGAT ACT AT G;
                CGAT GGT AAAGT AT TT C AACT CAGGT T GGAT ACCT CT CGAAG
ACCCAGAGT AT T GCGAATT AT GCCAGCT AT GAGGT AAAGT GT CAT AGCACCA
ACGT T AATT AAATT AAATT AAAAAAGGAAAT AT ACT AAAAT G;
                CGAT GGT AAAGT ATTT C AACT CAGGT T GGAT ACCT CT CGAAG
ACCCAGAGT AT T GCGAATT AT GCCAGCT AT GAGGT AAAGT GT CAT AGCACCA
ACGT T AATT AAATT AAATT AAAAAAGGAAAT AT ACT AT G;
                CGAT GGT AAAGT ATTT C AACT CAGGT T GGAT ACCT CT CGAAG
ACCCAGAGT AT T GCGAATT AT GCCAGCT AT GAGGT AAAGT GT CAT AGCACCA
ACGT T AATT AAATT AAATT AAAAAAGGAAAT CGCGAT ACT AAAAT G; and
                CGAT GGT AAAGT ATTT C AACT CAGGT T GGAT ACCT CT CGAAG
ACCCAGAGT AT T GCGAATT AT GCCAGCT AT GAGGT AAAGT GT CAT AGCACCA
ACGT T AATT AAATT AAATT AAAAAAGGAAAT CGAT ACT AAAAT G.
```

Appropriate modifications to this expression control sequence may be made to obtain even higher levels of protein expression when the sequence is used as part of an expression system. This sequence may be modified by methods such as (1) site specific mutagenesis [see B. A. Ooostra et al., *Nature*, 304, 456–459 (1983)]; (2) site manipulation at the ClaI site, (e.g., use of a Klenow fragment to fill in nucleotides or a Sl/Bal digestion to delete nucleotides); and (3) insertion of synthetic oligonucleotide fragments. In particular, we have found that the ClaI site or the segment ATXATG may be modified. Such modified sequences and similarly modified sequences may be substituted for this sequence in the recombinant DNA molecules, hosts, and methods of the present invention and are all considered to be within the scope of the present invention. Similarly, the aforementioned techniques for modifying this sequence are applicable to converting a particular sequence of this sequence into a different sequence. Also, one skilled in the art may choose different combinations of bases within the definition of X to optimize expression levels in particular situations or to confer other desirable properties upon the recombinant DNA molecules of the present invention.

Use of the pL-T4 results in high expression of TNF-like polypeptides. The recombinant DNA molecules comprising the $P_L$ promoter are advantageously used to transform hosts carrying the λ repressor. In one embodiment of the present invention, the expression control sequence described above is inserted downstream of a $P_L$ promoter [see H. Bernard et al., Gene, 5, 59–76 (1979), and European Patent Application Number 81.301413.1, Publication Number 041767].

Useful expression hosts may include well known eukaryotic and prokaryotic hosts, such as strains of *E.coli*, such as *E.coli* HB 101, *E.coli* W3110, *E.coli* X1776, *E.coli* X2282, *E.coli* DHI(λ), and and *E.coli* MRCl, *Pseudomonas, Bacillus*, such as *Bacillus subtilis, Streptomyces*, yeasts and other fungi, animal, such as COS cells and CHO cells, and human cells and plant cells in tissue culture.

Of course, not all host/expression vector combinations function with equal efficiency in expressing the DNA sequences of this invention or in producing the TNF-like polypeptides of this invention. However, a particular selection of a host/ expression vector combination may be made by those of skill in the art after due consideration of the principles set forth herein without departing from the scope of this invention. For example, the selection should be based on a balancing of a number of factors. These include, for example, compatibility of the host and vector, toxicity of the proteins encoded by the DNA sequence to the host, ease of recovery of the desired protein, expression characteristics of the DNA sequences and the expression control sequences operatively linked to them, biosafety, costs and the folding, form or any other necessary post-expression modifications of the desired protein.

Furthermore, within each specific expression vector, various sites may be selected for insertion of the TNF-related DNA sequences of this invention. These sites are usually designated by the restriction endonuclease which cuts them. They are well recognized by those of skill in the art. It is, of course, to be understood that an expression vector useful in this invention need not have a restriction endonuclease site for insertion of the chosen DNA fragment. Instead, the vector could be joined to the fragment by alternative means. The expression vector, and in particular the site chosen therein for insertion of a selected DNA fragment and its operative linking therein to an expression control sequence, is determined by a variety of factors, e.g., number of sites susceptible to a particular restriction enzyme, size of the protein to be expressed, susceptibility of the desired protein to proteolytic degradation by host cell enzymes, contamination or binding of the protein to be expressed by host cell proteins difficult to remove during purification; expression characteristics, such as the location of start and stop codons relative to the vector sequences, and other factors recognized by those of skill in the art. The choice of a vector and an insertion site for a DNA sequence is determined by a balance of these factors, not all selections being equally effective for a given case.

The TNF and TNF-like polypeptides produced by fermentation of the prokaryotic and eukaryotic hosts transformed with the DNA sequences of this invention, and, less preferably, the native TNF or TNF-like polypeptides purified by the processes of this invention or produced from the amino acid sequences of those polypeptides are useful in a variety of compositions and methods for anticancer and antitumor treatment and therapy. They are also useful in antimalarial therapy and methods.

Administration of these polypeptides, or perhaps peptides derived or synthesized from them or using their amino acid sequences, or their salts or pharmaceutically acceptable derivatives thereof, may be via any of the conventionally accepted modes of administration of agents which exhibit anticancer, antitumor or antimalarial activity- These include oral, parenteral, subcutaneous, intravenous, intralesional or topical administration. Local, intralesional or intravenous injection is preferred.

The compositions used in these therapies may also be in a variety of forms. These include, for example, solid, semisolid and liquid dosage forms, such as tablets, pills, powders, liquid solutions or suspensions, suppositories, injectable and infusable solutions. The preferred form depends on the intended mode of administration and therapeutic application. The compositions also will preferably include conventional pharmaceutically acceptable carriers and may include other medicinal agents, carriers, adjuvants, excipients, etc., e.g., human serum albumin or plasma preparations. Preferably, the compositions of the invention are in the form of a unit dose and will usually be administered one or more times a day. The amount of active compound administered at one time, or over the course of treatment, will depend on the subject being treated, the severity and course of the tumor or cancer or malarial infection, the manner and form of administration, and the judgment of the treating physician. However, an effective dose may be in the range of from about 0.005 to about 5 mg/kg/day, preferably about 0.05 to about 0.5 mg/kg/day; it being recognized that lower and higher doses may also be useful.

Accordingly, this invention provides a method of treatment for cancer or tumors in mammals, including humans, comprising the administration of an oncologically effective amount of a compound of the invention or its pharmaceutically acceptable salts or derivatives. It should, of course, be understood that the compositions and methods of this invention may be used in combination with other cancer or tumor therapies, e.g., together with interferons, e.g., IFN-α, IFN-β and IFN-γ, or chemotherapy, for the treatment of cancers and tumors in mammals.

According to another aspect of this invention, mammals are treated with pharmaceutically effective amounts of TNF and an antibiotic in combination, for a period of time sufficient to suppress or inhibit tumor growth, and preferably to kill tumor cells. The mammals preferably are treated with a composition comprising a combination of TNF and actinomycin D. Alternatively, they can be treated sequentially with the two components. However, the particular sequence of treatment chosen does not appear to be important. More specifically, mammals may be treated with subcutaneous, intravenous intramuscular or intralesional injections of between about 10 μg to 100 mg of TNF per patient per day. However, this dosage should be adjusted by the treating physician according to recognized medical standards, to accommodate the physical condition and acceptance level of the patient. In accordance with this invention, they may also be treated with a pharmaceutically effective amount of a antibiotic before, concurrently, of after treatment with TNF [see A. Goodman et al., *The Pharmacological Basis of Therapeutics*, pp. 1290–91 (1980)]. Actinomycin should be administered by intralesional injection into the tumor.

The TNF-like compounds of this invention may also be useful as antiparasitic agents. For example, it is known that the human malaria parasite, *Plasmodium falciparum* is sensitive to TNF [Playfair et al., *Imm. Today*, 5, pp. 165–166 (1984)].

In order that our invention herein described may be more fully understood, the following examples are set forth. It should be understood that these examples are for illustrative purposes only and should not be construed as limiting this invention in any way to the specific embodiments recited therein.

Example 1: In Vivo Induction And Assay Of TNF-Like Compounds

There are many methods known to induce TNF production in animals. Infection of the animal with agents, such as, BCG, corynebacteria, and Zymosan (from the walls of yeast saccharomyces cerevisae), induce massive hyperplasia of the reticuloendothelial system (RES) in vivo. Endotoxin, derived from the cell walls of bacteria (such as LPS from *E.coli*), may then be used to trigger the release of TNF by the activated macrophages.

To induce TNF-like production for subsequent use in the processes of this invention, we chose to use rabbits. However, we could also have chosen various other animals, such as, mice, rats, dogs, monkey, cattle, etc. Alternatively, established cell lines (human, mouse, etc.) can be used (infra). In our preferred embodiment using rabbits, we injected the rabbits intravenously with an inoculum of $4 \times 10^7$ viable BCG organisms. We used BCG because it is known to provide maximal stimulation of the RES system and maximal sensitization to endotoxin [E. A. Carswell et al., "An Endotoxin-Induced Serum Factor That Causes Necrosis of Tumors", *Proc. Natl. Acad. Sci USA*, 72, p. 3666 (1975)]. About 14 days later, when the RES was sufficiently stimulated, we injected each rabbit intravenously with 100 μg LPS to trigger the production of TNF. We exsanguinated the animals 2 h later and pooled the serum of the treated animals.

To select an appropriate target cell for our TNF assay, we examined the sensitivity of a variety of human cell lines for the cytotoxic effect of in vitro induced human TNF and in vivo induced rabbit TNF. As summarized in Table I, all of the human transformed cell lines that we tested were more sensitive to TNF activity than the non-transformed human cells that we tested. And at 37° C., the sensitivity for human TNF of all of the non-transformed cell lines tested (182 PF, E15M, WISH, HEK) lay below 10% of the sensitivity of L-929 cells at 37° C. It was also of interest that one matched pair (A) ($tu^-$ and $tu^+$) of hybrids originating from Hela cells fused with a normal fibroblast cell line showed the tumorigenicity correlated with sensitivity towards a necrotizing factor. However, no difference could be seen in the second pair of such hybrids (B). Furthermore, because the human cells tested by us are more sensitive to human TNF than to rabbit TNF, we believe that there is a degree of species specificity in the action of TNF.

TABLE I

| | Cytotoxic Effect Of TNF On Human Cells | | | |
|---|---|---|---|---|
| | 37° C. | | 39.5° C. | |
| Cells[a] | Rabbit[b] | Human[c] | Rabbit | Human |
| L-929 | 100[d] | 100 | 300 | 250 |
| KB | 10 | 100 | 15 | 125 |
| SV80 | 2.4 | 200 | 3.7 | 150 |
| Hela | 3.7 | 100 | 11.1 | 150 |
| VA4 | 7.5 | 25.6 | 3.75 | 12.8 |
| VA13 | 12.5 | 75 | 25 | 50 |
| HOS | 2.5 | 12.8 | 5 | 38.4 |
| MNNG-HOS | 2.0 | 25 | 4.2 | 50 |
| Hep | 1.9 | 12.8 | — | — |
| $tu^-$ | 0.8 | 3.7 | 1.2 | 11.1 |
| $^A tu^+$ | 1.2 | 100 | 1.2 | 100 |
| $tu^-$ | 1.2 | 11.1 | 3.7 | 100 |
| $^B tu^+$ | 0.4 | 11.1 | 1.23 | 33.3 |
| 182PF | <0.05 | <3.7 | <0.05 | <3.7 |
| FS4 | <0.05 | <6.3 | <0.05 | <3.7 |
| E1SM | 0.5 | 6.3 | 0.5 | 8.4 |
| WISH | <0.05 | <3.7 | <0.05 | <3.7 |
| HEK | 0.5 | 6.3 | 0.5 | 6.3 |

[a]L-929: mouse fibrosarcoma; KB: human epidermoid carcinoma; SV80: SV40-transformed human fibro-blasts; Hela: human, epitheloid carcinoma, cervix; VA-4: SV40-transformed human lung; VA-13: SV40-transformed human lung; HOS: human osteosarcoma; MNNG-HOS: chemically transformed osteosarcoma; Hep: human epidermoid carcinoma, larynx; $tu^-$: tumor suppressed hybrid (Hela × Hum. fibrobl. (GM0077)); $tu^+$: in vivo revertant of $tu^-$ (E. J. Stanbridge et al, Science, 215, pp. 252–259 (1982)); 182PF: human skin hereditary adenomatosis of colon and rectum (normal skin biopsy); FS4: human diploid fibroblast; E1SM: human diploid fibroblast; WISH: human amnion; HEK: human embryonic kidney.
[b]serum of BCG- and LPS- injected rabbits
[c]growth medium of human placental M0 stimulated in vitro with γ-IF (24 hrs) and LPS (3 hrs)
[d]expressed as a percentage of the sensitivity of the L-929 cells at 37° C.

Because the L-929 cells displayed one of the highest specific tumor-correlated sensitivities towards the necrotizing factor that is evidence for TNF activity, we chose and prefer those cells for our assay. For the assay, we used essentially the method described by Ruff et al., *Lymphokine Reports*, Vol. II (1980).

We first prepared serial dilutions of the presumed TNF-containing fraction and added the L-929 cells (50,000 cells/well) and actinomycin D to a final concentration of 1 μg/ml. This mixture was incubated at 37° C. or 39.5° C. for 18 h (at the higher temperature the L-929 target cells are 2.5 to 3.0 times more sensitive than at the lower temperature). At the end of the incubation period, we stained and counted the cells. Alternatively, we dissolved the stained cells in 33% HOAc and measured the released dye using a Kontron Spectrophotometer (577 nm).

In our assay, a TNF Unit (U) per ml represents the reciprocal of the dilution of TNF required to reduce cell survival 50% within 18 h in the killing assay performed in the presence of actinomycin D.

Example 2: Induction Of TNF Or TNF-Like Activity In Established Cell Lines

TNF or TNF-like activity can also be induced in vitro in established cell lines. For the induction of human TNF, for example, we chose the human monocytic U-937 cell line (Human histiocytic lymphoma, C. Sundstrom and K. Nilsson, Int. J. Cancer, 17, pp. 565–77 (1976)). However, other human pre-monocytic cell lines (e.g., HL-60, Mi-1), human monocytic cell lines (e.g., TPH-1, J-111) or human macrophages isolated, e.g., out of placentas, could as well have been used by us to induce our human TNF-like polypeptides. It should, of course, be understood that each of those in vitro sources of human TNF may require a more or less specific induction scheme for optimal production of TNF or a TNF-like compound.

In our chosen embodiment for the induction of human TNF, we grew our U-937 cell line in roller bottles in RPMI-1640 medium, enriched with 5% non-inactivated pre-selected batches of fetal calf serum (FCS, Gibco, Paisley, Scotland) and 5% horse serum (Gibco). When the cells reached a density of $1.5 \times 10^6$ cells/ml, we induced them for 24 h with 32 nM TPA (Sigma, St. Louis, Mo., U.S.A.) in RPMI-1640, 0.1 U/ml bovine crystalline insulin (BDH, Poole, England), 50 nM retinoic acid (Calbiochem, Frankfurt, West Germany), 1% giant tumor cell (GTC)-conditioned medium (Gibco), 0.5 mg/ml Cytodex 3 (Pharmacia, Uppsala, Sweden) in spinner flasks at a density of $1 \times 10^6$ cells/ml.

In our chosen embodiment for the induction of mouse TNF, we chose the mouse tumor macrophage cell line PU.5.1.8 [*Cancer Res.*, 37, pp. 546–550 (1977)]. However, we could as well have selected other mouse macrophage cell lines, such as J-774, RAW 309, and WR 19 M. We induced the PU 5.1.8 cell line to produce TNF essentially as described by Männel et al., *Inf. and Imm.*, 30, pp. 523–30 (1980). In general outline, we grew the cells in RPMI-1640 medium, enriched with 10% FCS (309 Gibco 011-6309), in roller bottles. We then induced the cells at a concentration of $3.5 \times 10^6$ cells/ml with 5 µg LPS/ml in RMPI-1640 for 4 h in the roller bottles.

We collected the in vitro induced cells (mouse or human) by centrifugation and used them as a source of mRNA containing the genetic information coding for TNF or a TNF-like polypeptide. We also used them as a source of mouse or human TNF itself.

Example 3: Preparation Of mRNA Containing Genetic Information Coding For TNF Activity We used the in vitro induced U-937 (human) or PU 5.1.8 (mouse) cells prepared above as a source of TNF-specific mRNA. We extracted total cytoplasmic RNA from the cells by lysing them in Nonidet P-40 and subsequently phenolizing the lysate. We then isolated the polyadenylated RNA (poly $A^+$ RNA) from the lysate by oligo dT-cellulose chromatography (Type 3, Collaborative Research). We further fractionated the poly $A^+$ RNA on a 15% frozen-thawed sucrose gradient (corresponding to a sucrose gradient of 5% to 20%) using a Beckman SW41 rotor, 4° C., 40K, and 19 h.

Figure 1B:
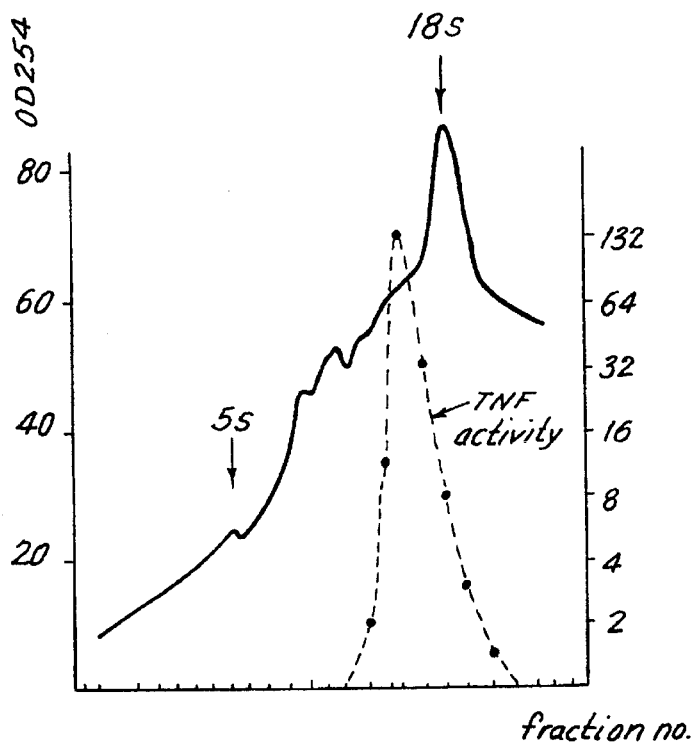

We assayed the biological activity of each fraction by microinjection of an aliquot into *Xenopus laevis* oocytes (50 pg mRNA per oocyte; 15 oocytes per sample). We then incubated the injected oocytes for 24 h in oocyte bathing medium (containing 0.1% polyethylene glycol 6000, 0.4% Aprotinin (Sigma), and 1 mM $CuSO_4$) and assayed the TNF activity in the medium on L-929 cells at 39.5° C. using our previously described in vitro assay system. In our assays, we observed a reproducible TNF biological activity in fractions corresponding to mRNA which sedimented at about 16S and 17S, respectively, for human and mouse TNF-related RNA. FIG. 1 depicts the OD-profile of two representative sucrose gradients of human and mouse mRNA preparations, respectfully.

Example 4: Construction Of Mouse and Human cDNA Banks

We constructed human and mouse cDNA banks, substantially as described by Wickens et al. "Synthesis Of Double-Stranded DNA Complementary To Lysosyme, Ovomucoid And Ovalbuman mRNAs", *J. Biol. Chem.*, 253, pp. 2483–95 (1978), using ±8 µg of those fractions of poly $A^+RNA$ which showed the maximum TNF biological activity after injection into oocytes. Of course, it should be understood that our cloned cDNA libraries could also have been prepared from poly $A^+RNA$-derived from other human or animal sources or from total cellular RNA without the described prior enrichment or size selection.

Although we might have used other conventional procedures, for example, those described by Land et al., "5-Terminal Sequences Of Eukaryotic mRNA Can Be Cloned With High Efficiency", *Nucleic Acids Research*, 9, pp. 2251–66 (1981); *Okayoma and Berg*, "High Efficiency Cloning Of Full-Length cDNA", *Mol. and Cell. Biol.*, 2, pp. 161–70 (1982); or *Maniatis et al.* in "Molecular Cloning" (ed. Cold Spring Harbor Laboratory, Cold Spring Harbor, N. Y.), pp. 229–46 (1982), we chose the following procedures for cDNA cloning.

a) First Strand Synthesis

For synthesis of the first cDNA strand, we used ±80 µg poly $A^+RNA$/ml, 50 mM Tris-HCl (pH 8.3), 50 mM KCl, 10 mMMgCl$_2$, 10 mMDTT, 0.5 mM of each dNTP, with 1/1000 dCTP replaced by $\alpha^{32}$P-dCTP at ±600 Ci/mmole (Amersham, Buckinghamshire, England), p(dT)10 at 60 µg,/ml (Pharmacia-PL Biochemicals, Uppsala, Sweden), 750 Units/ml human placental RNAse inhibitor (Amersham), and 1000 Units/ml AMV reverse transcriptase (Anglian Biotechnology Ltd, Colchester, England).

For the reaction we used a total volume of 100 µl, 41° C., and 1 h. We subsequently extracted the reaction mixture twice with a mixture of phenol/ chloroform/isoamylalcohol (25/24/1), twice with diethylether, and precipitated the DNA by adding 1 vol 4 M NH$_4$OAc and 4 vol of ethanol. We repeated the precipitation twice. If necessary, we also added yeast tRNA to the reaction mixture as a carrier before we added the ethanol.

b) Removal Of The RNA Template And Second Strand Synthesis

We redissolved the precipitated DNA in 60 µl 15 mM potassium phosphate (pH 6.9), 0.25 mM EDTA, added 2 µg RNAse A (Boehringer Mannheim, West Germany) and 250 units RNAse T1 (BRL, Neu-Isenburg, West Germany) and allowed the mixture to stand at 37° C. for 30 min.

We then heated the mixture in a boiling water bath for two min and immediately quenched it on ice. We then added potassium phosphate buffer (pH 6.9) (up to a final concentration of 100 mM), MgCl$_2$ (up to a final concentration of 10 mM), DTT (up to a final concentration of 10 mM), dNTP's (up to a final concentration of 1 mM each), and 330 U/ml *E.coli* DNA polymerase I (endonuclease-free) (Boehringer Mannheim, West Germany). We carried out our second strand synthesis at 15° C. for 6 h in a total volume of 300 µl. We then stopped the reaction by the addition of EDTA (pH 8) to a final concentration of 25 mM and extracted and precipitated the mixture, as above.

We redissolved the pellet in 80 µl of a mixture of 50 mM Tris-HCl (pH 8.3), 50 mM KCl, 10 mM MgCl$_2$, 10 mM DTT, 1 mM of each dNTP, and 650 U/ml AMV reverse transcriptase (Anglian Biotechnology Ltd, Colchester, England) and incubated the mixture at 41° C. for 90 min in order to boost the efficiency of second cDNA synthesis. We then again isolated the DNA by extraction and precipitation, as described above.

c) S1 Nuclease Treatment

We dissolved the DNA pellet in 80 μl of a buffer containing 125 mMNaCl, 25 mMNaOAc, 1 mM zinc acetate (pH 4.5), added 20 Units S1-nuclease (BRL, Neu-Isenburg, West Germany) and let the mixture stand for 20 min at 37° C. We stopped the reaction by addition of EDTA (pH 8) to a final concentration of 20 mM and neutralized the reaction mixture by addition of Tris-HCl (pH 8) to a final concentration of 200 mM. We then again extracted and precipitated the DNA, as described above, redissolved it in a buffer containing 30 mMNaCl, 10 mM Tris-HCl-1 mM EDTA (pH 8) and size fractionated it on a Sepharose CL 4B column (0.8×12 cm) (Pharmacia Fine Chemicals, Uppsala, Sweden), equilibrated against the same buffer. We collected fractions of two drops each and we pooled those fractions containing DNA of at least 500 base pairs, or larger, and precipitated the pooled fractions, as described above.

d) Tailing Of Double Stranded cDNA And PstI-Restricted pAT153

We tailed our double-stranded cDNA with oligo-dC tails using the following reaction mixture: ±2.5 μg double-stranded cDNA/ml, 100 mM potassium cacodylate (pH 7.2), 2 mM $CoCl_2$, 200 uM DTT, 40 uM deoxy-(5-$^3$H)-cytidine triphosphate (17 Ci/mmole, Amersham, Buckinghamshire, England), 400 units/ml terminal deoxynucleotidyltransferase (Pharmacia-PL Biochemicals, Uppsala, Sweden). We continued the reaction at 37° C. until 12–18 dC residues were incorporated per 3'OH end and then stopped the reaction by the addition of EDTA (pH 8) to a final concentration of 20 mM. We then immediately extracted the material with phenol, then with diethylether (twice), and precipitated the tailed cDNA, as described above.

We also added oligo dG-tails to a PstI restricted plasmid pAT153* under similar conditions except that (1) we replaced the deoxy-(5-$^3$H)-cytidine-5'-triphosphate with deoxy-(8-$^3$H)-guanosine-5'-triphosphate (25 Ci/mmole, Amersham, Buckinghamshire, England) at a concentration of 4 μM, and (2) we used a concentration of linearized plasmid DNA of ±16 pmole/ml.

e) Annealing Of Oligo dC-Tailed Double-Stranded cDNA With Oligo dG-Tailed Vector DNA We annealed our dC-tailed double-stranded cDNA and dG-tailed linearized plasmid essentially according to the method of *Maniatis et al.* in "Molecular Cloning" (ed. Cold Spring Harbor Laboratory, Cold Spring Harbor, N.Y.), p. 242 (1982), except that after heating the mixture to 65° C., we cooled it to room temperature over a 2 to 3 h period.

f) Transformation Of E.coli Strain DH1 (λ)

We next transformed *E.coli* DH1 (λ) [Hanahan, "Studies On Transformation Of *Escherichia coli* With Plasmids", *J. Mol. Biol.*] with our annealed recombinant DNA using 10 ng of vector-DNA per 100 μl of competent cells. We then plated the transformation mixtures on Millipore HATF (0.45 μM pore size) filters (Millipore Corp., Bedford, Massachusetts) that were layered on top of Luria broth agar plates, containing 10 μg/ml tetracycline. After propagation of the colonies, we placed the filters on fresh plates also containing 20% glycerol and stored them at −20° C.

Using this protocol, we obtained a human cDNA bank of about 60,000 clones and a mouse cDNA bank of about 30,000 clones. * We restricted pAT153 (a well Known and available cloning vector) with PstI according to the conditions of the supplier (Boehringer Mannheim, West Germany), except that we used three times as many enzyme units.

Example 5: Purification Of TNF From Rabbit Serum

Figure 2:
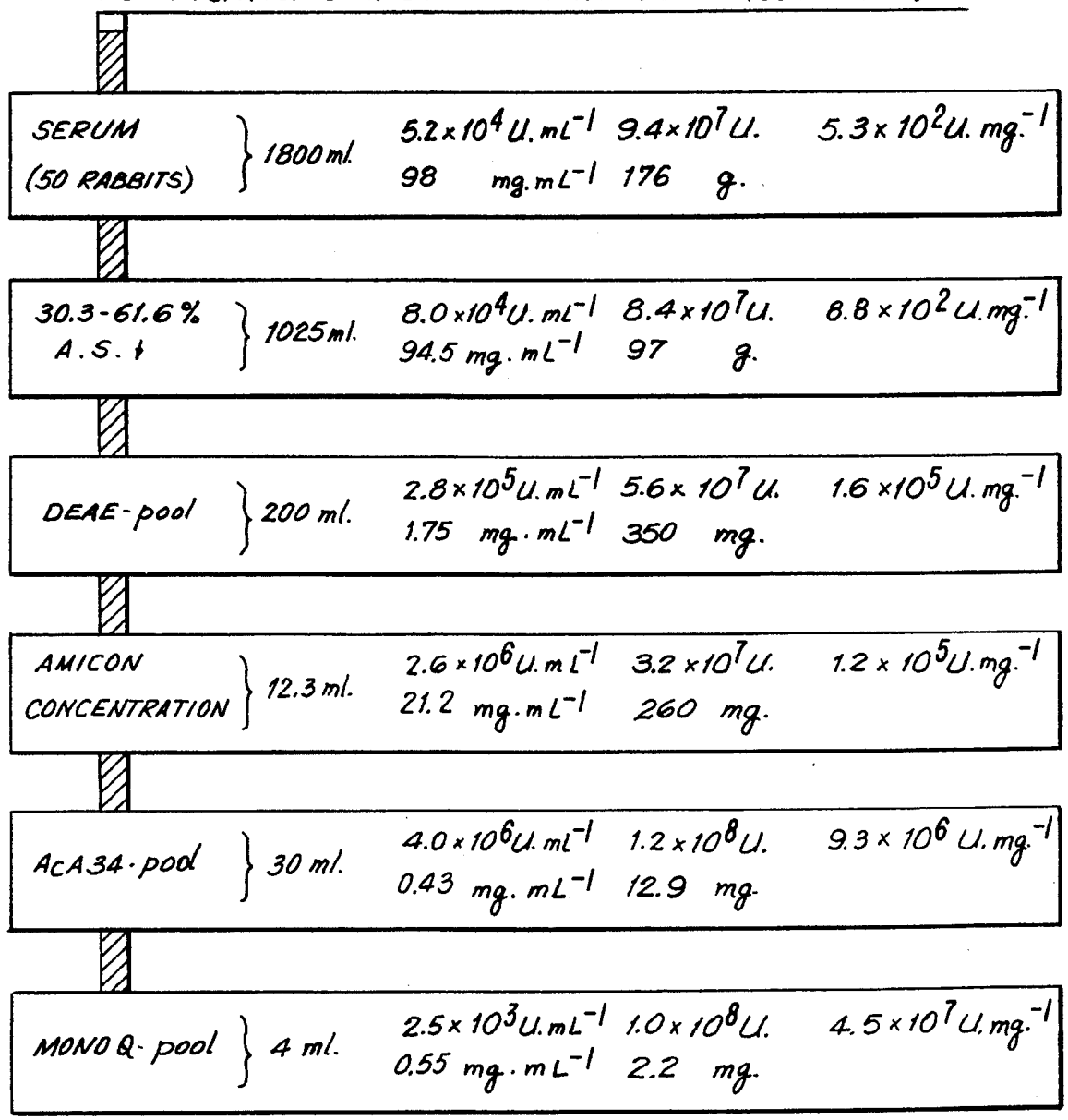
FIG. 2 depicts in schematic outline one embodiment of a process according to this invention for purifying TNF-like polypeptides from induced rabbit. serum.

Referring now to FIG. 2, we have depicted therein a schematic outline of one embodiment of a process of this invention for purifying TNF-like polypeptides from induced rabbit serum. As illustrated in the embodiment of our invention depicted in FIG. 2, we pooled the serum of 50 rabbits that we had treated as described in Example 1. In a typical experiment, after intravenous injection of LPS, the serum of the BCG-treated rabbits (1800 ml) contained about $5.2 \times 10^4$ U TNF/ml, with a specific activity of about $5.3 \times 10^2$ U TNF/mg of protein.

a) Precipitation Of Protein From Rabbit Serum

We first saturated the isolated rabbit serum with solid ammonium sulphate, by adding the sulphate slowly (about 6 grams/min) with constant stirring at 4° C. until we reached an ammonium sulphate saturation of 35.9%. We then maintained the pH at 7.0 with ammonia and kept the solution at 4° C. with constant stirring for about 18 h. We next removed the precipitate from the solution by centrifugation (30 min, 7500 rpm, 4° C. in a Beckman JA 7.5 rotor). We then added ammonium sulphate to the supernatant under the same conditions until a saturation of 61.6% was reached. After 5 h of constantly stirring the above-described saturated serum, we again collected the precipitate, as described above, and resuspended the pellet from this second precipitation in 600 ml 50 mM Tris-HCl (pH 7.5) at 4° C. We then dialyzed the solution for 40 h against 4×3000 ml 50 mM Tris-HCl (pH 7.5) (4° C.) to remove the ammonium sulphate. This process resulted in a 760 ml protein solution in 50 mM Tris-HCl (pH 7.5). We identified this 35.9%–61.6% ammonium sulphate fraction as Fraction A.

Because the pellet from the 0–35.9% ammonium sulphate fraction also contains a considerable amount of TNF activity, we resuspended it in about 200 ml 50 mM Tris-HCl (pH 7.5) and dialyzed this solution for 18 h against 2000 ml of a 30.8% ammonium sulphate solution at 4° C. under constant stirring. After removing the precipitate by centrifugation, as before, we dialyzed the supernatant against 3×2000 ml 50 mM Tris-HCl (pH 7.5) at 4° C. under constant stirring for 3×2½ hours. This dialysis resulted in a 270 ml protein solution in 50 mM Tris-HCl (pH 7.5). We designated this 30.8%–35.9% ammonium sulphate fraction as Fraction B.

We combined Fractions A and B and after centrifugation (30 min, 7500 rpm, 4° C. in a Beckman JA 7.5 rotor), we passed the solution through a 0.45 μm nitrocellulose filter (Millipore, Bedford, Massachusetts) to afford a 1025 ml 30.8%–61.5% ammonium sulphate fraction. This combined fraction contained about $8.0 \times 10^4$ U TNF/ml— substantially all of the TNF activity of the rabbit serum— and only 55% of its total protein. The specific activity of the fraction was $8.8 \times 10^2$ U TNF/mg of protein.

b) Ion-exchange Chromatography (Mild Alkaline pH)

We separated the TNF activity in our combined fraction from the many other proteins in it by making use of TNF's strong binding affinity to an anion exchanger. While many anion exchange chromatographic systems are well known to those skilled in the art, we chose to use a DEAE-Sephacel column, 2.6 cm in diameter × 48 cm (Pharmacia, Uppsala, Sweden). It should, of course, be understood that other anion exchange columns could also have been chosen without departing from the scope of this invention.

We heavily overloaded our chosen column, previously eguilibrated with 50 mM Tris-HCl (pH 7.5), with our TNF-containing solution, loading the solution at a flow rate of 0.8 ml/min. Because the TNF competed out other previously bound proteins on the column, this procedure resulted in a column that had substantially all of the TNF in the solution bound to it. After washing the column with one column volume 50 mMTris-HCl (pH 7.5) and one column volume 0.1 M NaCl in 50 mM Tris-HCl (pH 7.5) at a flow rate of 0.8 ml/min, we eluted it with a linear salt gradient from 0.1 M to 0.4 M NaCl in 50 mM Tris-HCl (pH 7.5) at the same flow rate. This elution afforded elution of the fractions containing TNF activity at the end of the 0.1 M NaCl wash step. As illustrated in FIG. 2, the resulting solution contained $2.8 \times 10^5$ U TNF/ml, specific activity $1.6 \times 10^5$ U/mg of protein. Therefore, this anion exchange step permitted us to remove over 99% of the non-TNF proteins, while retaining substantially all of the TNF activity.

c) Concentration Of The Ion-Exchange Pool

Referring again to FIG. 2, we next pooled and concentrated the TNF-containing fractions eluted from the DEAE-Sephacel column. We centrifuged the pooled fractions (30 min, 13,500 rpm, 4° C. in a Beckman JA 14 rotor) and then concentrated the supernatant approximately 17-fold with an Amicon TCF-2 apparatus (we pressurized the cell to 1.5 atm and used a Diaflo UM 10 membrane (Amicon, Danvers, Massachusetts, U.S.A.)). The resulting concentrate contained $2.6 \times 10^6$ U TNF/ml and had a specific activity of $1.2 \times 10^5$ U/mg (FIG. 2).

d) Gel Filtration

We next fractionated the concentrate, prepared as described above, according to molecular weight using gel filtration. While a number of suitable gel filtration systems are well known to those skilled in the art, we chose to use an AcA 34 gel (LKB, Bromma, Sweden) with a fractionation range from 20,000–350,000 daltons. Again, it should be understood that other filtration systems could also have been used.

We suspended our chosen gel in 1 M NaCl and 50 mM Tris-HCl (pH 7.5), poured the gel into a column (2.5 cm in diameter × 89 cm), and equilibrated the column with the same buffer at a flow rate of 0.5 ml/min. Before loading the TNF concentrate onto the prepared AcA 34 column, we equalized the salt concentration of the Amicon concentrate with the salt concentration of the colE buffer using a 5 M NaCl solution in 50 mM Tris-HCl (pH 7.5). The gel filtration fraction of this process that had the TNF activity corresponded to a molecular weight of approximately 35,000 daltons.

As shown in FIG. 2, the 30 ml of solution remaining after gel filtration contained $4.0 \times 10$ U TNF/ml and had a specific activity $9.3 \times 10$ U TNF/mg of protein. This represents an approximately 20,000fold TNF purification from serum.

e) Ion-Exchange Chromatography (Slightly Acidic pH)

We next dialyzed the pooled gel filtration fractions containing TNF activity overnight at 4° C. against 2×750 ml 0.1 M NaCl in 20 mM histidine-HCl buffer (pH 5.8). Then, after having eguilibrated a preparative mono-Q column (1 cm in diameter × 11 cm, Pharmacia, Uppsala, Sweden) with the same buffer, we fractionated the dialized, TNF-containing solution on this column using a linear gradient from 0.1 M to 0.4 M NaCl in 20 mM histidine-HCl buffer (pH 5.8). The fractions containing the TNF activity eluted in the gradient at about 0.26 M NaCl (Fractions 15 and 16). Referring again to FIG. 2, these chromatographic steps afforded 4 ml of a solution containing $2.5 \times 10^7$ U TNF/ml and having a specific activity of approximately $4.5 \times 10^7$ U TNF/mg of protein. This fraction represented an approximately 100,000-fold TNF purification from serum.*

Figure 3:
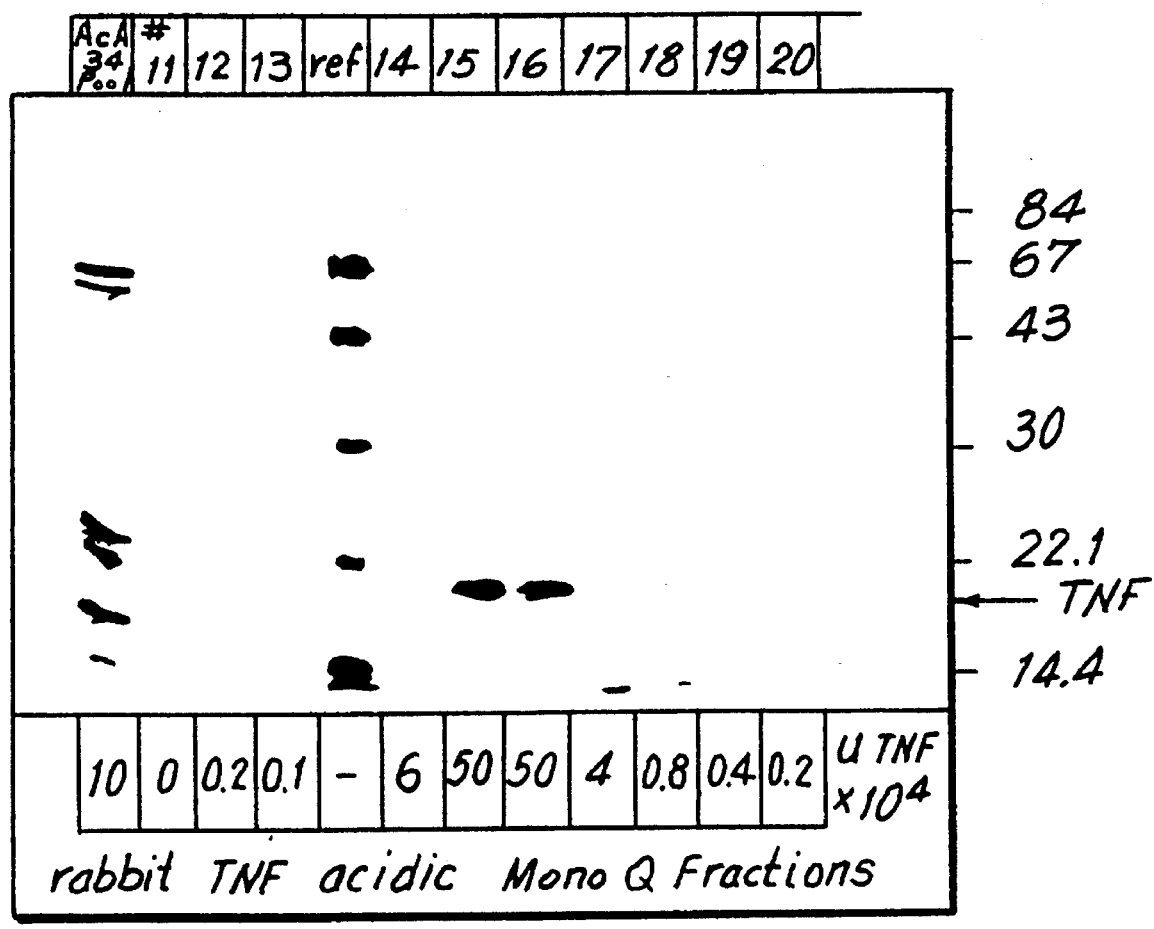
FIG. 3 depicts an SDS-PAGE (12%) analysis of rabbit TNF purified from induced rabbit serum in accordance with one embodiment of the purification process of this invention.

We analyzed the eluted fractions from the acidic mono Q column on SDS-PAGE (12%). Referring now to FIG. 3, we observed that a single protein band is conserved in the active column fractions at a position equivalent to a molecular weight around 18,000 daltons. The intensity of the Coommassie Brilliant Blue (Serva R250) staining in this band correlates precisely with the TNF activity of the corresponding column fractions. Although SDS-PAGE denatures proteins, the TNF activity eluted from the gel slices of a non-denaturing gel afforded the same band upon electrophoresis on an SDS-polyacrylamide gel, thereby confirming that the 18,000 dalton band does represent a TNF-like polypeptide.

Example 6: Determination Of The Amino Acid Sequence Of Portions Of Purified Rabbit TNF And Construction Of Various DNA Probes Having purified this TNF-like polypeptide from induced rabbit serum, we used it to determine portions of its amino acid sequence. It should also, however, be understood that our purified TNF may be employed clinically to study the effects of TNF on cancer and tumors and malarial infections and in therapy against them. Our purified TNF may also be used to produce TNF antibodies (polyclonal or monoclonal) by injection of the purified protein into * Fluctuations in total TNF activity, as depicted in FIG. 2, are due to the inaccuracy (by a factor of up to two) of our TNF activity assay. appropriate animals. See, e.g., B. Benacerraf and E. Unanue, "Textbook of Immunology", Williams & Wilkins (Baltimore, Maryland), pp. 12–22 (1979). These antibodies are then useful, for example, in assays and in purification processes for TNF itself.

Techniques for determining the amino acid sequences of proteins and peptides derived from them are well known in the art. We chose one of those available automated techniques to determine the amino acid sequence of selected portions of the rabbit TNF-like compound purified in Example 5. We first prepared CNBr fragments of our purified rabbit TNF under standard conditions. We then separated those fragments on a gel, electroeluted the individual bands, dialized them and applied them directly to an Applied Biosystems Gas Phase Sequencer (Model 470).

Referring now to the FIGS. 4 and 5, we have depicted therein the amino acid sequence of two portions of our purified rabbit TNF polypeptide (TNF CNBr-fragments 3 and 4). Also depicted in those figures are various DNA codons that code for each of the amino acids in the two fragments. The various codons represent a degenerate set that codes for the determined amino acid sequences. Because of the degeneracy of the genetic code, numerous DNA probes containing the many possible nucleotide permutations may be synthesized for a given amino acid sequence. It is, of course, preferable to select for DNA probe synthesis an amino acid sequence containing amino acids with the least degenerate codons. However, when a long enough probe is chosen, any possible mismatches will be compensated for by regions of perfect match so that detectable hybridization will still occur, even in highly degenerate sets of probes.

The amino acid sequences that we have derived from our purified rabbit TNF are useful in synthesizing nucleotide (DNA) probes for use in screening a variety of DNA libraries to select related DNA sequences by hybridization. These selected sequences may then be manipulated for the expression of TNF in prokaryotic and eukaryotic hosts transformed with them. They are also useful as screening probes to select other related DNA sequences that code for mammalian TNFs, e.g., mouse and human TNFs.

We are also able to employ our purified TNF and the synthetic peptides based on its amino acid sequences to prepare polyclonal or monoclonal antibodies to TNF in appropriate animals. These antibodies are then useful in the purification of TNF and in the radioimmunoassay of TNF, including use in the direct selection of TNF-expressing clones produced by the processes of the invention. Furthermore, our purified protein and synthetic peptides are useful for clinical evaluations of TNF activity in tumor, cancer and malarial therapy and in those therapies and related methods.

Turning again to the FIGS. 4 and 5, we have depicted therein various sets of degenerate TNF DNA probes that we synthesized using conventional phosphoamide DNA synthesis techniques on the basis of the amino acid sequences that we determined for TNF fragments 3 and 4. See, e.g., *Tetrahedron Letters*, 22, pp. 1859–62 (1981). For example, based on the amino acid sequence of TNF fragment 3 ranging from Lys (AA #2) to Ala (AA #12), we synthesized four 32-mers (RAB TNF3-I to RAB TNF3-IV) having nucleotide permutations in positions 4-6-19-21. See FIG. 4, the permutations are underscored. We also constructed a longer overlapping probe of 60 oligonucleotides. See FIG. 4.

Based on our amino acid sequence of TNF fragment 4 ranging from Trp (AA #3) to Leu (AA #9), we synthesized four degenerate sets of 20-mers (RAB TNF4-A1 to RAB TNF4-A4). See FIG. 5. These 20-mers had a nucleotide permutation at position 12 (underscored in FIG. 5). Based on subsequent hybridization patterns in Southern blots of genomic rabbit DNA with our different sets probes, we subdivided the RAB TNF4-A2 probe into 3 groups based on a nucleotide permutation at position 15 (see FIG. 5, permutation is underscored). Based on the amino acid sequence ranging from Phe (AA #13) to Asp (AA #19) of fragment 4, we also constructed a second set of six 20-mers (RABTNF4-B1 to RAB TNF4-B6). Finally, we prepared a long overlapping probe, extending over almost the whole known amino acid sequence of this portion of our TNF protein. See FIG. 5.

Before using our DNA probes for screening, we 5' end-labelled each of the single-stranded DNA probes with T4 polynucleotide kinase. We labelled the longer overlapping probes to high specific activity (>10$^8$/μg probe DNA) by filling in using Klenow polymerase in the presence of all four α$^{32}$P-deoxynucleoside triphosphates.

Example 7: Screening Of A Rabbit Genomic Library

While any DNA collection may be usefully screened with one or more of our DNA probes, it is usually preferred to screen first a DNA library derived from the same animal as was used for the isolation of the polypeptide on which the synthetic DNA probe was based. Using a DNA library from the same animal permits the hybridization conditions to be more stringent because the homology between the probe and the corresponding regions in the genomic DNA will be high. Using the same animal source for both the DNA probe and the DNA library is particularly important when short DNA probes are used. It is correspondingly less important when larger DNA probes are used. After a DNA is selected by screening with such short probes, it, either alone or in the form of a recombinant phage or plasmid, may then be used to select by hybridization related DNAs in DNA libraries derived from that same animal or from other animals, including humans. Because the selected DNA is longer than the original synthetic probes used for its isolation, and therefore more likely to contain regions of perfect matching, we prefer to use the short synthetic probes to select DNA sequences from the same species and to use the DNAs selected with those probes to select inter species DNAs.

In accordance with the above principles, we screened a cloned library of rabbit genomic DNA, essentially constructed according to the procedures of Maniatis et al., "The Isolation Of Structural Genes From Libraries of Eukaryotic DNA", *Cell*, 15, pp. 687–701 (1978).

For our library, we plated a total of about 6×10$^5$ phages and sequentially lifted them onto two nylon filters (PAL) (using respectively 5 and 8 min adsorption times). After denaturation, neutralization and fixation of the phage DNA on the filters, we screened the library with a high specific activitylabelled (0.5–1.0×10$^7$ cpm/pmole DNA) synthetic nucleotide probe RAB TNF3-III (FIG. 4) (this probe being chosen on the basis of preliminary analyses by Southern digestion and hybridization). We prehybridized the filters in 4 × SSC, 15 mM sodium phosphate (pH 7), 10 × Denhardt's solution, 250 μg/ml t-RNA and 7% SDS at 50° C. for 2 h. After washing, we hybridized them with the labelled probe in 10% dextran sulfate, 5 × SSC, 10 x Denhardt's solution, 20 mM sodium phosphate (pH 7), 500 μg/ml t-RNA and 7% SDS at 50° C. overnight. After washing the filters at 50° C. in 2 × SSC, 1% SDS, we assayed the filters photographically.

As a result of this screening, we obtained 16 double positive hybridization clones. We isolated the corresponding plaques from these sixteen positive clones and analyzed their DNA by Southern blots using DNA probes derived from both TNF fragments 3 and 4. In one of those analyses, we observed that Southern blots of EcoRI restriction digests of the DNA of the 16 phages with oligonucleotide probe RAB TNF3-III and RAB TNF4-A2-3 afforded one phage that contained an EcoRI band that hybridized with both probes. Because this particular clone contains DNA segments that hybridize to probes corresponding to both fragment 3 and fragment 4 of our TNF-related polypeptide, we concluded that it very likely contained most or if not all of the rabbit TNF gene.

Example 8: Plus-Minus Screening Of cDNA Mouse And Human Libraries

We based this screening approach on the use of two types of human and mouse DNA probes in parallel, one being cDNA synthesized from the sucrose gradient fractions of poly A$^+$RNA which showed maximum TNF biological activity after oocyte injection (see Example 3), the other being cDNA synthesized on an equivalent fraction(s)

obtained from uninduced cultures. The first was called the plus probe, the latter the minus probe.

We synthesized cDNA for the plus and minus probes essentially as described in Example 4, Section a, except that we used only 0.2 mM deoxynucleoside triphosphates and we added $\alpha^{32}$P-dATP (7000 Ci/mmole, Amersham, Buckinghamshire, England) to a concentration of 2 µM.

We used the plus and minus, mouse and human, probes in parallel to screen two sets of randomly selected replicas of our cDNA libraries derived from mouse and human sources, respectively (see Example 4). We prepared the replicas of our cDNA libraries according to the method of Hanahan and Meselson "Plasmid Screening At High Colony Density", *Gene*, 10, pp. 63–67 (1980). We lysed the bacterial colonies on the filters (Millipore, HATF, 0.45 µm), substantially as described by *Maniatis et al.* in "Molecular Cloning" (ed. Cold Spring Harbor Laboratories, Cold Spring Harbor, N.Y.), pp. 326–28 (1982).

For our hybridization screening of these libraries we used the homologous probe, i.e., we used the mouse plus and minus probes for screening the mouse cDNA library and the human plus and minus probes for screening the human library. And we only investigated further those clones in each library that were positive with the plus probe, but not with the minus probe.

As a result of the above described plus/ minus screening of a mouse library of 5000 clones randomly selected from our 30,000 clone library, we selected 55 positive clones for further analysis. The results of the plus/minus screening of the human library were ambiguous. Accordingly, we did not further pursue this plus/minus screening of the human cDNA library. Instead, we screened our human cDNA library as described infra.

Example 9: Isolation Of Mouse And Human TNT-Specific cDNA Clones a) Isolation Of Mouse TNF-Specific cDNA We picked the selected 55 cDNA clones, described above in the plus/minus screening, and grew them up individually. We then isolated the plasmid DNA from overnight cultures (grown in 5 ml Luria broth, 10 µg/ml tetracycline), substantially as described by H. C. Birnboim and J. Doly, *Nucl. Acids. Res.*, 7, pp. 1513–23 (1979), and 11 groups of 5 clones each were used for further study. We separated, the insert DNAs from these groups of plasmids using Pst I restriction, followed by agarose gel electrophoresis. We subsequently transferred the insert DNAs from these 11 groups of clones and fixed them to nitrocellulose membrane filters (0.45 µm, Millipore), substantially as described by E. M. Southern, *J. Mol. Biol.*, 98, pp. 503–17 (1975).

We then screened the filter-bound DNAs using the long overlapping probes derived from rabbit TNF Fragments 3 and 4, described previously. See FIGS. 4 and 5. For this hybridization screening, we first prehybridized the filters at 42° C. overnight in 20% formamide (deionized using a mixed bed resin), 5 × SSC, 5 × Denhardt's solution, 5 mM EDTA, 50 mM sodium phosphate buffer (pH 6.5) and 20 µg/ml *E.coli* DNA (denatured by boiling for 7 min and sonicated using an MSE Soniprep 150 sonicater, 3×1 min, 25–30 µ). We then incubated the filters at 42° C. for 40 h in the presence of the labelled probe DNAs (see Example 6) (denatured by boiling for 7 min), 20% formamide (deionized using a mixed bed resin), 5 × SSC, 5 × Denhardt's solution, 5 mM EDTA, 25 mM sodium phosphate buffer (pH 6.5), and 20 µg/ml *E.coli* DNA (prepared as before). After washing the filters twice for 1 h at 35° C. in the presence of 2 × SSC and 0.1% SDS, we analyzed them photographically.

One group (Group 6) afforded one positive clone using the probe derived from Fragment 3. Accordingly, we then screened the 5 individual members of this group, substantially as described above, and isolated two positive clones—both identical. We designated this clone p-mTNF-1.

We then screened our collection of 55 positive plus/minus clones with an RsaI fragment of p-mTNF-1, that we had first radioactively labelled by nick translation, and selected two other positive clones— p-mTNF-2 and p-mTNF-3.

We then confirmed that all three of these clones were able to select TNF-active mRNA from our poly A$^+$RNA. To do this, we picked the selected clones and grew them up individually. We then isolated plasmid DNA from overnight cultures (grown in 400 ml Luria broth, 10 µg/ml tetracycline), substantially as described by *Pulleyblank et al.*, "A Method For The Purification Of *E. coli* Plasmid DNA By Homogeneous Lysis And Polyethylene-Glycol Precipitation", *Molec. Biol. Rep.* 9, pp. 191–95 (1983).

We then purified approximately 30 µg of each preparation on a NACS 32 Prepack column (BRL, Neu-Isenberg, West Germany) using the conditions recommended by the supplier, precipitated the DNA with ethanol, redissolved it, cleaved it with Eco RI (Boehringer Mannheim, West Germany) phenol-extracted it and reprecipitated it.

We then bound the digested plasmid DNA to a membrane, essentially as described by Kafatos et al., "Determination Of Nucleic Acid Sequence Homologies And Relative Concentrations By A Dot Hybridization Procedure" *Nucl. Acid. Res.*, pp. 1541–52 (1979), except that (1) we used a Gene screen (New England Nuclear, Boston, Mass.), instead of nitrocellulose filters; (2) we increased the ammonium acetate concentration from 1 M to 2 M; and (3) we did not bake the filters under vacuum, but treated them instead with UV, substantially as described by Church and Gilbert, *Proc. Natl. Acad. Sci. USA*, 81, pp. 1991–95 (1984).

We then screened the filter bound, EcoRI digested plasmid DNAs by hybridization with poly A$^+$ RNA (from the sucrose gradient fractions which previously had shown maximum TNF activity after oocyte injection, see Example 3). We eluted the bound RNA, essentially as described by Parnes et al., "Mouse β2 Microglobulin cDNA Clones: A Screening Procedure For cDNA Clones Corresponding To Rare mRNAs", *Proc. Natl. Acad. Sci. USA*, 78, pp. 2253–57 (1981), except that (1) we eluted the RNA in the presence of 5 µg poly A$^-$ RNA (oligo dT cellulose run-through) and (2) instead of phenolizing, we precipitated the RNA twice.

We injected the recovered RNA into *Xenopus laevis* oocytes, as described in Example 3, and, after the proper incubation period (see also Example 3), we assayed the medium for TNF-activity, as described in Example 3. Using the above-described hybrid selection, we determined that the inserts of p-mTNF-1, p-mTNF-2 and p-mTNF-3 each selected TNF-active RNA from our poly A$^+$RNA.

Figure 6:
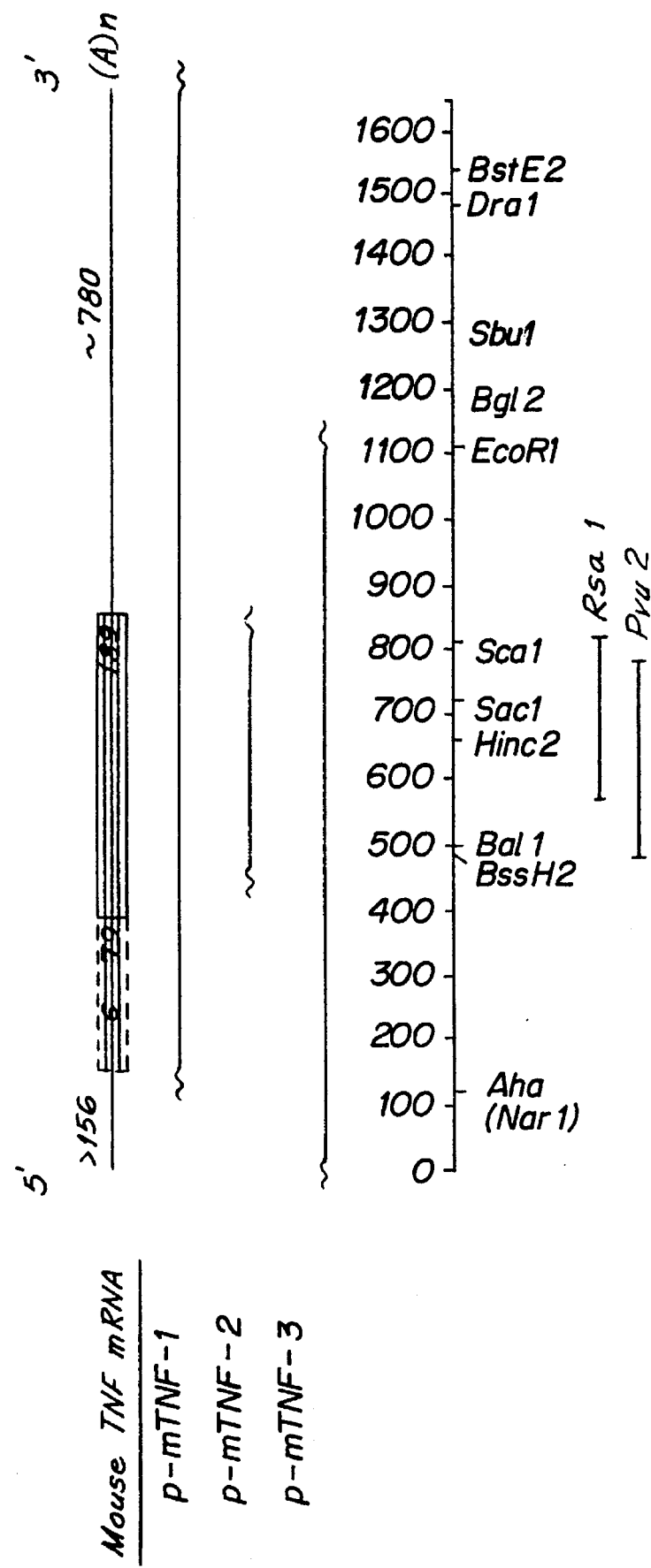
FIG. 6 depicts the general structure of mouse TNF RNA and the position of the cDNA of clones p-mTNF-1, p-mTNF-2 and p-mTNF-3.

We next analyzed our three mouse TNF clones by restriction analysis. See FIG. 6. Such analysis demonstrated that the 3 clones were derived from the same RNA and hence from the same gene. A detailed restriction map of these clones is depicted in FIG. 6. The three clones had TNF-related inserts of about ±1550, ±350 and ±1000 base pairs, respectively.

We also determined the complete cDNA sequence of a composite insert from p-mTNF-1 and p-mTNF-3, using the Maxam-Gilbert technique [A.M. Maxam and W. Gilbert,

*Proc. Natl. Acad. Sci. USA*, 74, pp. 560–64 (1977)]. This sequence and the amino acid sequence derived from it is depicted in FIG. 7.

Referring now to FIG. 7, we have depicted the nucleotide sequence of the 1644 nucleotides of a composite TNF related DNA sequence that we derived from the sequencing of clones p-mTNF-1 and p-mTNF-3. (The cDNA insert of clone p-mTNF-1 included a 3' non-coding region and extended up to the ATG start codon (see FIG. 7). The cDNA insert of p-mTNF-3 included the entire coding sequence for mouse pre-TNF and a portion of the 5' non-coding region. See FIG. 6. The sequence is numbered from nucleotides 1 to 1644. The full boxes (ATG and TGA designate the start and stop codons of the putative mouse pre-TNF. The dashed boxes (nucleotides 1614–19 and 1630–35) represent putative AAUAAA polyadenylation signals. A continuous reading frame exists between the start codon (ATG) and the stop codon (TGA). The amino acids coded for by the codons in that reading frame are designated beneath those codons using conventional, single letter designations. The putative signal sequence of mouse TNF (as determined by comparison with the partial N-terminal amino acid sequence of human TNF, described infra) is designated by dashes under those amino acids. It should, however, be recognized that because mouse TNF has a two amino acid deletion, as compared to human TNF, at or near to the N-terminus of the mature protein, our assignment of leucine aS the first N-terminal amino acid of mature mouse TNF (FIG. 7) is subject to confirmation by protein sequencing of purified native mouse TNF, as described for human TNF. The putative mature TNF sequence in FIG. 7 is designated by a solid line. The full boxes in this amino acid sequence designate a glycosylation signal (N-X-S/T) and two cysteine (C) residues which we believe are involved in a disulphide bridge.

(b) Isolation Of A Human

TNF-Specific cDNA Clone

In order to select a human TNF-specific cDNA clone, we first grew a set of our human TNF cDNA clones (that we had randomly selected from our library of 60,000 cDNA clones, supra) on nitrocellulose filters (0.45 μm diameter, Millipore) and lysed them and fixed them to the filters substantially as described by D. Hanahan and M. Meselson, *Gene*, 10, pp. 63–67 (1980). We screened this library using a PvuII-PvuII restriction fragment from our mouse TNF cDNA (p-mTNF-1) (this fragment overlaps with a part of the coding region for mature mouse TNF, see FIGS. 6 and 7). We purified this DNA fragment by agarose gel electrophoresis and radiolabelled it by nick translation, substantially as described by P.W.J. Rigby et al., *J. Mol. Biol.*, 13, pp. 237–51 (1977). For this hybridization, we used conditions that were substantially the same as those that we used to isolate our mouse TNF-specific cDNA clone p-mTNF-1.

Although we noted a relatively high background on the colonies, one clone afforded a significantly more intense signal. We confirmed this result by Southern hybridization, as described previously. We designated this clone as p-hTNF-1. From a genomic human DNA library (prepared substantially as described for our rabbit genomic bank, supra), we also selected a number of positive clones with the same PvuII-PvuII probe.

Figure 8:
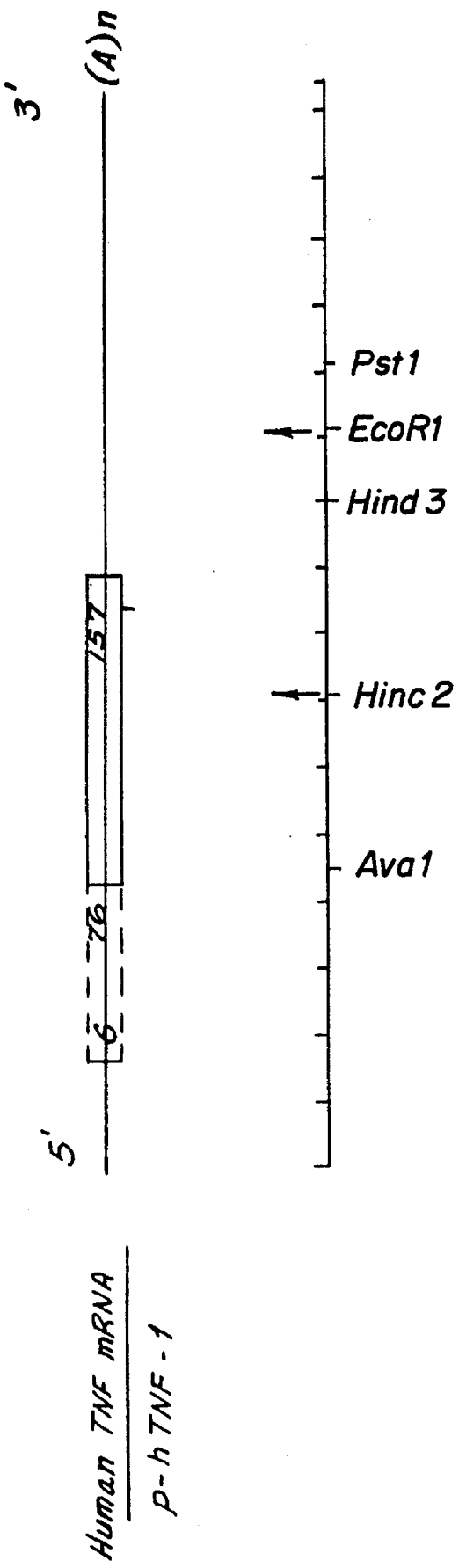
FIG. 8 depicts the general structure of human TNF RNA and the position of the cDNA of clone p-hTNF-1.

Referring now to FIG. 8, we have depicted a partial restriction map of p-hTNF-1. The TNF-related insert in p-TNF-1 is about 1650 base pairs long, about the size necessary to correspond to a full size cDNA derived from the 16S human TNF mRNA fraction.

Referring now to FIG. 9, we have depicted the nucleotide sequence of the 1606 nucleotides of the cDNA insert of p-hTNF-1. The sequence is numbered from nucleotides 1 to 1606. The full boxes (ATG and TGA) designate the start and stop codons of the putative human pre-TNF. A continuous reading frame exists between the start codon (ATG) and the stop codon (TGA). The amino acids coded for by the codons in that reading frame are designated below the codons using conventional three letter abbreviations. The putative signal sequence of human TNF (as determined by comparison with the partial N-terminal amino acid sequence of native human TNF purified from induced U937 cells (infra)) is designated by dashes under those amino acids. The mature human TNF is designated by a solid line. Mature human TNF is believed to be non-glycosylated. This belief is supported by the absence of a glycosylation signal in our human TNF coding sequence. There are, however, two cysteines (C) in our mature human TNF amino acid sequence. We believe these cysteines are involved in disulphide bridge formation.

Example 10: Expression Of Human TNF-Like Polypeptides In Eukaryotic Cells

In order to express our human TNF cDNA coding sequence in eukaryotic cells, we chose pSV529 as an expression vector (D.Gheysen and W. Fiers, *J. Mol. Appl. Genet.*, 1, pp. 385–94 (1982)). This vector contains an expression unit consisting of the SV40 late promoter followed by the splice signals of the major 16S late mRNA, a unique Bam HI restriction site, and a polyadenylation signal. The vector also contains the complete SV40 early region (small t and large t antigens) and the SV40 "ORI" for DNA replication and "enhancer" sequences so that optimal replication and expression in permissive Cos cells is obtained. As described previously, we could, of course, have chosen any of a large number of useful and well known expression vectors for expressing our cDNA.

We chose Cos cells [Y. Gluzman, *Cell*, 23, pp. 175–82 (1981)) for a eukaryotic expression host. These cells contain an integrated, ORI-defective SV40 mutant and permit replication of SV40-derived vectors up to 100,000 copies per cell as a result of the constitutive t-antigen production. Again, we could have chosen any of a number of eukaryotic expression hosts that are compatible with our chosen expression vector for expression of our human TNF cDNA sequences. For example, we could have used AP8 cells (Gheysen and Fiers, supra) or other monkey cells permissive for SV40 replication.

We inserted the human TNF cDNA coding sequence into pSV529 by first restricting p-hTNF-1 with PstI. We then purified the resulting PstI fragment, which includes the complete coding region of pre-human TNF, by agarose gel electrophoresis and blunt-ended the 3' protruding ends of the fragment using the Klenow large fragment of *E.coli* DNA polymerase I. We then added BglII oligodeoxynucleotide linkers (Collaborative Research) using T4 ligase, and restricted the DNA with BglII. We then inserted the BglII restricted DNA into the BamHI site of pSV529 using T4 ligase in the presence of BglII and BamHI.

From this ligation, we obtained both orientation of the TNF insert with respect to the SV40 late promoter— pSV529-hTNF(Pst)-I (sense orientation with respect to the SV40 late promoter) and pSV529-hTNF(Pst)-2 (anti-sense orientation).

We then transfected the recombinant expression vectors into our Cos cells as follows. Starting with a subconfluent monolayer, we seeded Cos 1 cells in DMEM (Gibco Cat.

No. 074-1600), containing 10% FCS (Gibco Cat. No. 011-6290) in 2 cm² wells (Becton Dickinson; Falcon Cat. No. 3047), at a density of 50,000 to 100,000 cells per well, and incubated them at 37° C., in the presence of 5% $CO_2$. Twenty hours later, we mixed DNA (1.5 to 3 μg/ml) with an equal volume of MEM (Gibco Cat. No. 071-1100), containing 5g/l HEPES (Sigma, Cat. No. H-3375) and 1 mg/ml DEAE-Dextran (MW ≅2,000,000, Pharmacia, Sweden). We then washed the cells twice with MEM-HEPES and covered them with 0,125 ml of the DNA-DEAE-Dextran solution. After incubation for 15–30 min at 37° C., we washed the cells twice with MEM-HEPES and added a solution of DMEM, 10% FCS (containing 0.1 mM chloroquine (Sigma, Cat. No. C-6628)) (see H. Luthman and G. Magnuson, *Nucl. Acids Res.*, 11, p. 1295 (1983)). We then incubated the cells for a further 4 h at 37° C., 5% $CO_2$. After washing the cells twice with DMEM, 10% FCS, and incubating them overnight (17 h) in DMEM, 10% FCS (containing 0.1 mM sodium butyrate (Sigma Cat. No. B-5887) (see C. Gorman and B. Howard, *Nucl. Acids Res.*, 11, p. 7631 (1983)), we again washed them twice with DMEM, 10% FCS, and incubated them further in 0.5 ml DMEM, 10% FCS, 37° C., 5% $CO_2$.

We took samples of the supernatant at 72 h and 96 h after DNA addition and assayed them on L929 cells (in the presence of 1 μg/ml Act. D) using 37° C. and 18 h for the assay. These assays demonstrated that transfection with pSV529-hTNF(Pst)-1 afforded 6400 U TNF/ml activity in the supernatant, while transfection with pSV529-hTNF-(Pst)-2 afforded no detectable TNF activity.

Example 11: Purification Of TNF From Human Cells

Referring now to FIG. 10, we have depicted therein a schematic outline of one embodiment of a process of this invention for purifying TNF-like polypeptides from the medium of U-937 cells induced for TNF production (see Example 2). As illustrated in the embodiment of our invention depicted in FIG. 10, we pooled the medium of several U-937 inductions at −80° C. until we had 65,000 ml, an amount we believed sufficient to afford enough human TNF for amino acid sequencing and antibody preparation. Our pooled solution contained about $3.0 \times 10^3$ U TNF/ml and had a specific activity of about $2.7 \times 10^4$ U TNF/mg of protein, TNF activity being determined as described previously. See Example 1.

(a) Concentration Of The TNF-Containing Medium

We thawed the medium in a warm room at 37° C. and as soon as it was thawed, we transferred it to a cold room (4° C.). We concentrated the 65000 ml pool approximately 80-fold with a Pellicon cassette system (Millipore, Bedford, Massachusetts). We successively passed our medium through a Pellicon membrane cassette with a nominal molecular weight limit (nmwl) of 100,000 daltons and a Pellicon membrane cassette of 30,000 daltons nmwl. Much of the TNF activity passed through the 100,000 daltons cassette, but was retained by the 30,000 daltons cassette. Then using diafiltration, we replaced the 30,000 daltons retentate medium with a 20 mM ethanol-amine-HCl (EA-Cl) (pH 9.0) buffer. After concentration and diafiltration, the 810 ml solution contained $6.0 \times 10^4$ U TNF/ml and had a specific activity of about $6.8 \times 10^4$ U TNF/mg of protein.

(b) Ion-Exchange Chromatography

We separated the human TNF activity of our concentrated medium from the many other proteins in it by making use of TNF's binding affinity to an anion exchange column. While many anion exchange chromatographic systems are well known to those skilled in the art, we chose to use a preparative mono-Q column (1 cm in diameter × 11 cm, Pharmacia, Uppsala, Sweden). A column of this size has a loading capacity of about 200 mg of protein. After having equilibrated the column with 20 mM EA-Cl (pH 9.0), we loaded 200 ml of our concentrate at a flow rate of 2 ml/min. We then fractionated the bound proteins using a linear gradient ranging from 0 M to 0.4 M NaCl in 10 mM EA-Cl (pH 9.0). The eluted TNF activity peaks around fraction 24 and is eluted at a salt concentration of about 0.16 M NaCl. We repeated this loading and gradient procedure reproducibly three times and pooled the fractions containing TNF activity. Our pooled fractions contained $3.0 \times 10^6$ U TNF/ml and had a specific activity of $1.1 \times 10^6$ U TNF/mg protein (see FIG. 10).

Because the amount of protein loaded in each run was just within the loading limits of our mono-Q column, resolution was not optimal. Accordingly, we decided to pass the TNF-containing pool from our first mono-Q column through another mono-Q column. we first dialyzed the pool overnight at 4° C. against 2×1000 ml 10 mM EA-Cl (pH 9.0). Then, having equilibrated the column with the same buffer, we fractionated the pool on the column by elution with a linear salt gradient from 0 to 0.2 M NaCl in 20 mM EA-Cl (pH 9.0). The resulting solution contained $1.1 \times 10^7$ U TNF per ml and had a specific activity of $2.3 \times 10^6$ U TNF/mg protein (see FIG. 10).

(c) Gel Filtration

We next fractionated our solution making use of differences in molecular weight. While a number of suitable gel filtration systems are well known to those skilled in the art, we chose to use a TSK-G 2000 SWG column (LKB, Bromma, Sweden) with a fractionation range for proteins from 500–60,000 daltons. We dialyzed our mono-Q pool overnight at 4° C. against 2×1000 ml 1M NaCl in 50 mMTris-HCl (pH 7.4) and reduced the volume of the dialyzate to 0.85 ml by rapid evaporation, using a Speed Vac Concentrator (Savant, Hicksville, N.Y.). After having equilibrated the gel filtration column with 1M NaCl in 50 mM Tris-HCl (pH 7.4), we passed the pool through the column at a flow rate of 1 ml/min. We detected TNF activity in the region where proteins of about 40,000 daltons are eluted. After this fractionation, our TNF-containing solution contained $3.4 \times 10^6$ U TNF/ml and had a specific activity of approximately $1.1 \times 10^7$ U TNF/mg of protein (see FIG. 10). This purification is a roughly 400-fold TNF purification from our U-937 cell medium.

We analyzed the fractionated pool on SDS-PAGE (12%). We observed a predominating band at a position equivalent to a molecular weight of about 17,000 daltons. We also observed a slower moving, weaker band at about 18000 molecular weight. These results strongly suggest that native human TNF may be composed of two protein subunits.

We used our purified human TNF to determine a partial N-terminal amino acid sequence. This sequence is depicted in FIG. 11. Changes to the sequence indicated as additions above, or deletions of, amino acids, were derived from the DNA sequence. We used that sequence to determine the putative signal sequence and mature coding sequence carried by our human TNF clone (supra).

Example 12: Expression Of Human TNF-Like Polypeptides In *E.coli*

Referring now to FIG. 12, we isolated a 669 base pair AvaI-EcoRI fragment from a partial cDNA clone that we had isolated from a conventionally prepared lambda gt 10 cDNA library prepared from poly A+ RNA isolated as described above from our induced U-937 cells (see Example 2). As depicted in FIG. 12, this fragment carries the coding information for amino acids 8–157 of mature human TNF (the codon for amino acid 8 (Pro) is the overhanging 5' end of the AvaI-restriction site). Although we isolated this AvaI-EcoRI fragment from a clone in our A gt10 cDNA library, we have isolated the same fragment from p-hTNF-1 using AvaI and EcoRI (see ExampLe 9(b)).

We next prepared a synthetic linker that encoded the first 7 amino acids of mature human TNF and included an overhanging 3' end complementary to the 5' end of our AvaI-EcoRI fragment (FIG. 12). We then ligated our synthetic linker to the AvaI site of our AvaI-EcoRI TNF fragment in the presence of T4 DNA ligase. We then filled in the EcoRI site with DNA polymerase (Klenow) in the presence of the 4 dNTPs. We then inserted the TNF-containing DNA fragment into expression vector $pP_r$-$T_7$(cop$^-$) (European patent application 101,061, published Mar. 28, 1984; ATCC 39189, deposited Sep. 15, 1982) that we had previously restricted with Sal I and blunt-ended with S1 nuclease (FIG. 12). This insertion operatively links the TNF coding sequence to the expression control system of $pP_r$-$T_7$(cop$^-$) directly to a codon (ATG) encoding methionine.

We transformed *E.coli* MC1061 with the resulting recombinant expression vector and selected appropriately transformed clones by hybridization to the synthetic linker that we had $^{32}$P-labelled. We then checked the selected clones by restriction digests.

We grew two selected clones (having the TNF sequence in the sense orientation with respect to the expression control sequence) $pP_r$-$T_7$(cop$^-$)- hTNF-1 and one selected clone (with the TNF sequence in the anti-sense orientation) $pP_r$-$T_7$(cop$^-$)-hTNF-2 overnight in 5 ml L Broth at 37° C. to an O.D.=3 (590 nm). We collected 1 ml of cells from each culture by centrifugation, resuspended them in 100 µl gel-loading solution (containing SDS, β-mercaptoethanol and urea), boiled the solution for 5 min, and loaded 30 µl onto a 15% SDS-polyacrylamide gel. We also collected a second 1 ml aliquot of cells from each culture, resuspended them in 0.4 ml PBS and added 10 µl of a 10 mg/ml solution of lysozyme. After allowing the cells to stand for 30 min at we subjected them to 3 freeze-thaw cycles to lyse them. We then diluted the cell lysates 10-fold in PBS and assayed them in L929 cells as described previously.

The clones in the sense orientation produced $8 \times 10^9$ U TNF/liter and those in the anti-sense orientation produced $5 \times 10^5$ U TNF/liter. Because our construction is characterized by an ATG start codon directly attached to the coding sequence of mature human TNF, we believe that the protein produced by our transformed cells is f-Met-TNF. However, it should be understood that the N-terminal methionine may be cleaved by the *E.coli* cells themselves during growth or production or be cleaved subsequently, if necessary or desirable, using enzymes described as being useful for that purpose.

Figure 13:
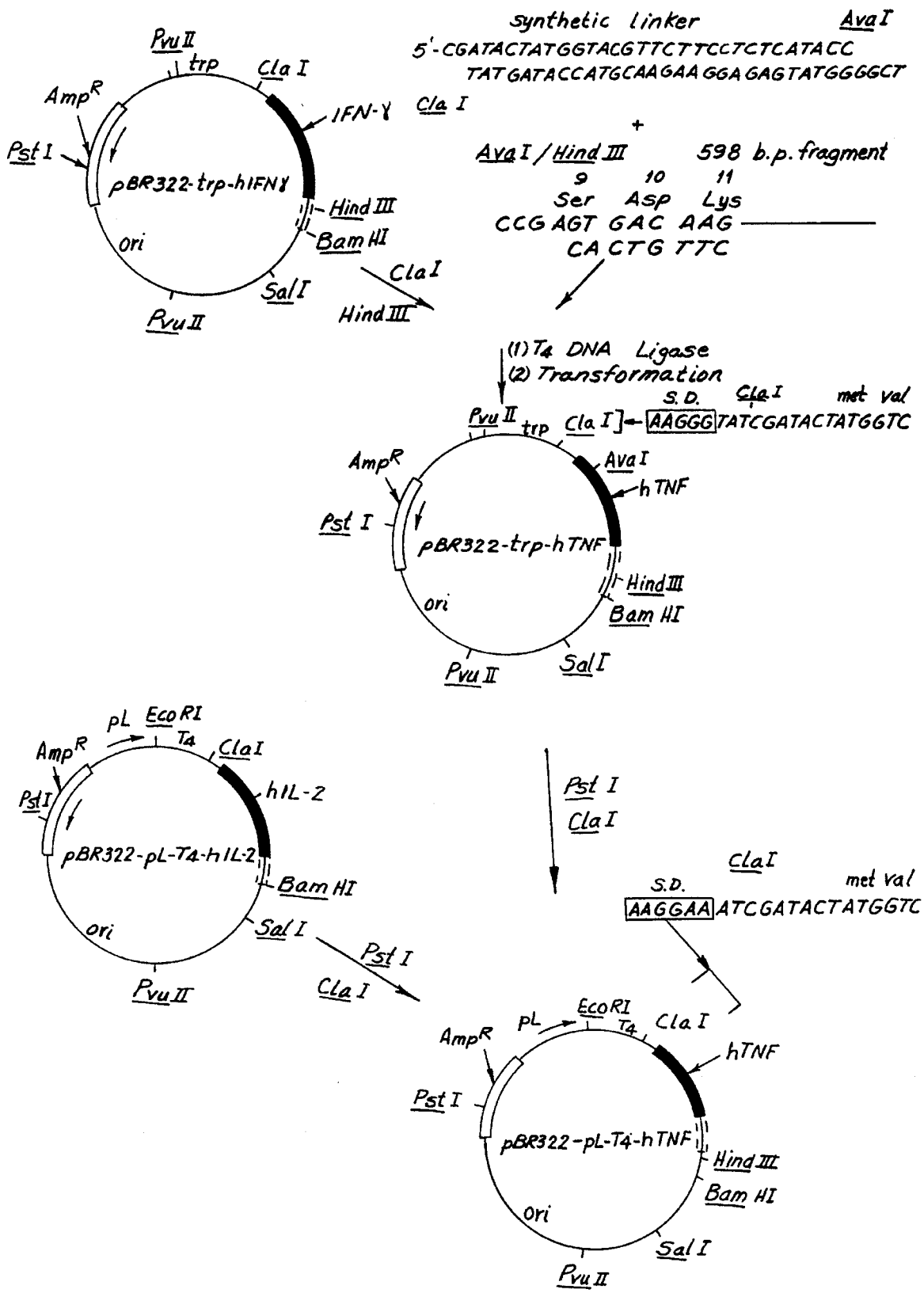
FIG. 13 depicts in schematic outline another embodiment of a process for constructing other recombinant expression vectors characterized by a DNA sequence coding on expression for human TNF.

In another preferred construction, for the production of a TNF-like polypeptide of this invention, we used a $\lambda P_L$-derived expression control sequence (see FIG. 13). For this construction, we first prepared and purified a 578 base pair Ava I-Hind III fragment of our DNA sequence encoding human TNF. This fragment encodes human TNF beginning at amino acid 8 of the mature sequence (FIG. 13). Again, although we isolated this TNF DNA fragment from a cDNA clone from our lambda gt 10 cDNA library (supra), we could have isolated it from p-hTNF-1 using those same restriction enzymes.

We next prepared a Cla I-Ava I synthetic linker that encodes the missing TNF amino acids (see FIG. 13). This fragment included an overlapping Ava I 5' end that is complementary to that of the 578 base ppair Ava I-Hind III TNF fragment. We also prepared and purified the larger Cla I-Hind III fragment of a plasmid designated pBR322-trp-IFN-γ (see FIG. 13).

After ligation of these three DNA fragments, we transformed an *E.coli* C600 strain with the resulting pBR322-trp-hTNF recombinant expression vector (FIG. 13). We then fermented the transformed host in a shake flask overnight at 37° C. in a rich, phosphate-buffered medium (glycerol, yeast extract, casamino acids). After fermentation, we lysed the cells in an SDS-urea buffer and analyzed the cell-produced proteins by SDS-polyacrylamide gel electrophoresis. We observed a band corresponding to hTNF activity on this gel. This activity represented about 10% of the total *E.coli*-produced proteins.

We then substituted a pL-T4 expression control sequence for the trp sequence in pBR322-trp-hTNF by isolating and purifying the smaller Pst I-Cla I restriction fragment (~1200 base pairs) of a plasmid designated pBR322-pL-T4-HIL-2 (FIG. 13). As shown in FIG. 13, this fragment contains a part of the gene coding for ampicillin resistance and the complete pL-T4 regulating sequence. In parallel, we also restricted pBR322-trp-hTNF with Pst I and Cla I and isolated and purified the larger fragment that contained the hTNF coding sequence. We then combined the two fragments to produce pBR322-pL-T4-hTNF (FIG. 13).

In order to assay for expression, we transformed an *E.coli* C600 strain with pBR322-pL-T4-hTNF harboring a λcts Kan$^R$ low copy number plasmid. On fermentation, (1.5 liters, 28° C., 24 h; then 42° C., 5 h) this construction produced about 30% TNF activity of the total *E.coli* proteins.

While we observed high expression of TNF-like polypeptides in our pL-T4 system, the product was a mutant TNF having histidine as the second amino acid instead of the native arginine. We do not know what caused the single base pair mutation that resulted in our mutant TNF. However, after site specific mutagenesis to the natural TNF (arg) sequence (a single base mutation) we observed no TNF expression with our construction. We suspect that some form of RNA secondary structure is responsible for this phenomenon.

Accordingly, we attempted several new constructions. Referring to FIG. 14, we constructed plasmid 153-pL-T4-hTNF-CA3(13) which includes pAT-153 deletion (rop-). This plasmid had a Cla I -Ava I ("CA") synthetic linker which codes on expression for the correct amino acid sequence (i.e., Arg instead of His) (see FIG. 14). It exists with or without the λcts repressor gene, described above. As indicated in FIG. 14, we deleted an Eco RI site at the pBR322, nucleotide 0 position. This plasmid demonstrated a high yield of TNF in transformed host *E.coli* W3110 (see Table II). However, our fermentation results have shown this construction to be unstable under storage conditions.

TABLE II

Plasmid: 153-pLT4 HTNF CA3

| Host strain | Scale | Growth Conditions | Expression level |
|---|---|---|---|
| K12 lambda | 1.5:1 | 37° C. 24 h | 4.3% |
| HB101 (BA) | 1.5:1 | 37° C. overnight | 8.6% |
| HB101 | 1.5:1 | 37° C. overnight | 7.3% |
| MC1061 | 1.5:1 | 37° C. overnight | 8.3% |
| E. coli B | 1.5:1 | 37° C. overnight | 9.9% |
| W3110 | 1.5:1 | 28° C. overnight, lysis | 22.0% |
| W3110 | 1.5:1 | 37° C. overnight, lysis | 18.0% |
| W3110 | 1.5:1 | 40° C. overnight | 11.7% |
| W3110 | 1.5:1 | 43° C. overnight | 10.2% |
| W3110 | 10.0:1 | 37° C. overnight | 10.4% |
| W3110 | 50.0:1 | 40° C. overnight | 11.3% |
| W3110 | 1.5:1 | 37° C. overnight | 15.1% |
| W3110 | 1.5:1 | 37° C. overnight | 0% |
| W3110 | 1.5:1 | 37° C. overnight | 5% |
| W3110 | 1.5:1 | 37° C. overnight | 0% |

We also created plasmid 153-pL-T4-hTNF-CA3-cts-T4-ter [DSM 3460] which had the λcts repressor gene. To create this plasmid we deleted the 3' noncoding region and included a synthetic T4 terminator at the H_in___dIII position. This plasmid also gave high expression but was more stable than 153-pL-T4-hTNF-CA3 (13) as a result of the T4 terminator (see FIG. 18). This plasmid should preferably be grown at 28° C., and after the addition of fresh medium, should be heat induced at 42° C.

Figure 16:
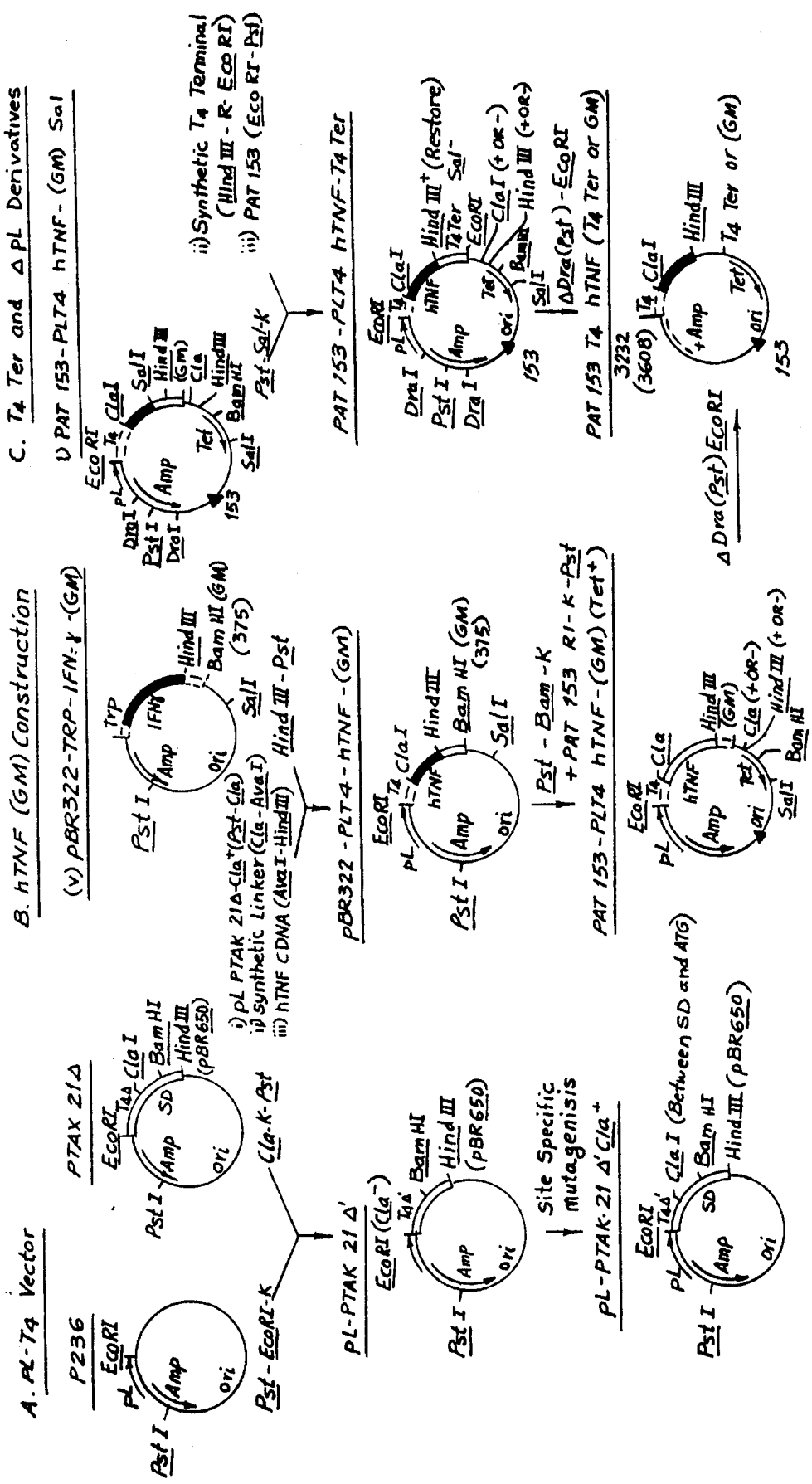
FIG. 16 depicts (A) the preparation of plasmid pL-pTAK-21Δ-CLA$^+$from plasmids p236 and pTAK 21Δ [K. Gorski et al., *Cell* (1985) (in press)]; (B) the construction of hTNF (G)n derivatives; and (C) the construction of T4-ter and ΔpL derivatives.
Figure 20B:
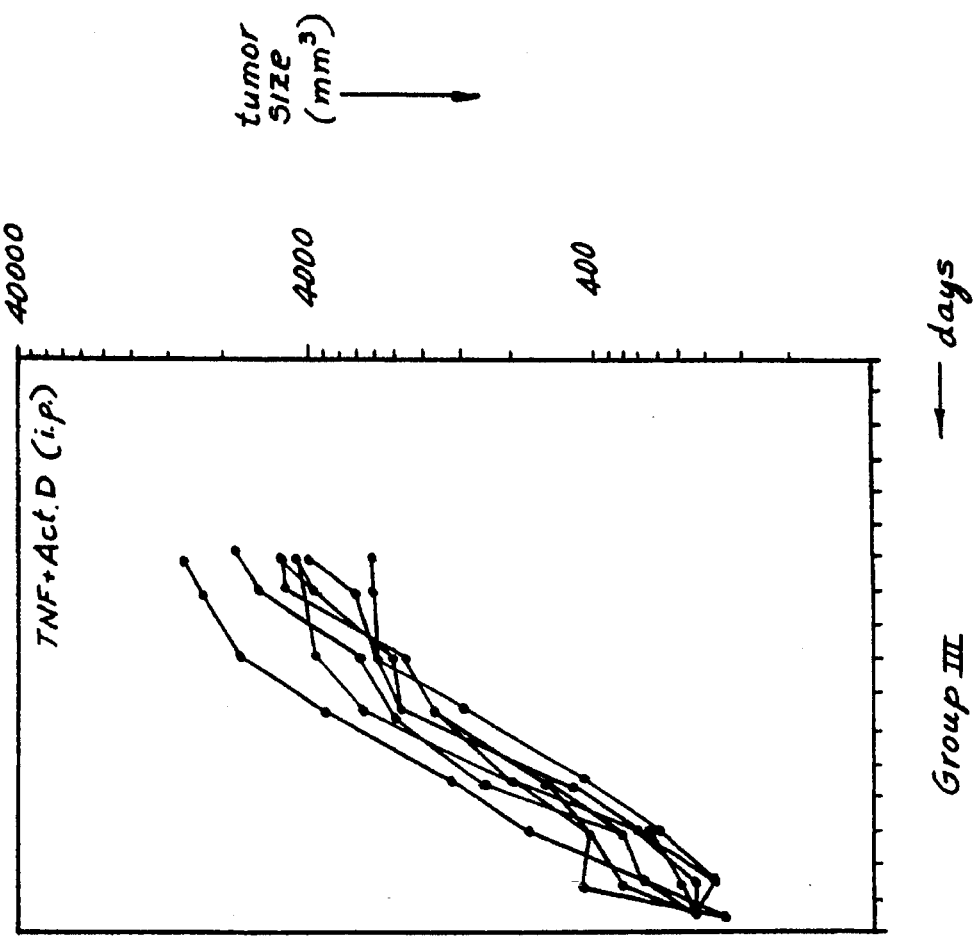
Figure 20A:
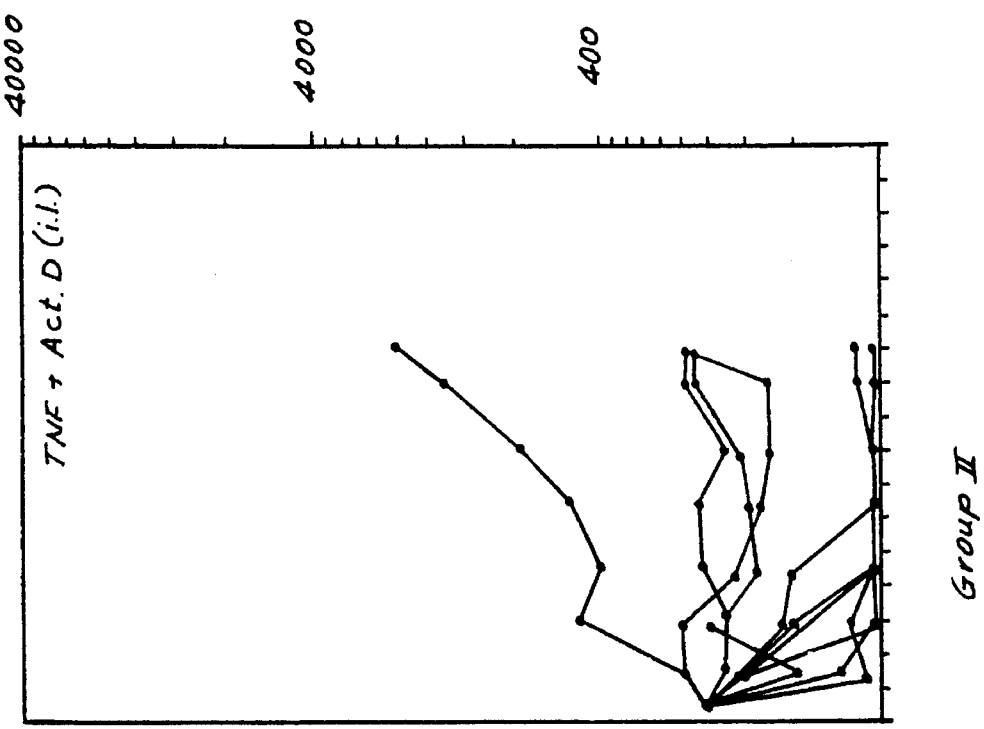

In a more preferred embodiment we constructed 153-T4-hTNF-CA5-T4ter [DSM 3461] which has a deleted pL portion, leaving only the T4 portion of the expression vector (see FIGS. 15, 16 and 17). As a result of the deletion, part of the sequence providing antibiotic resistance to ampicillin was lost. We therefore added an antibiotic resistance marker for tetracycline resistance at the end of the gene, before removing the $P_L$ sequence. Our more preferred plasmid has a C5 synthetic linker. This linker codes for the first seven amino acids (up to the AvaI site) of the natural TNF, and has the following sequence:

```
CGAT ACT AAA ATG GTC AGA TCA TCT TCT CGA ACC
GCT ATG ATTT TAC CAG TCT AGT AGA AGA GCT TGG
          Met Val Arg Ser Ser Ser Ang Thr
```

Also, the T4-terminator had an effect on the level of expression. This resulted in a high expression vector producing over 25% TNF in host strain WA802 (See Table III).

TABLE III

Plasmid: 153-T4-hTNF CA5 T4ter

| Host Scale | Scale | Growth conditions | Expression level |
|---|---|---|---|
| W3110 | 1.5:1 | 37° C. overnight | 25.0% |
| W3110 | 1.5:1 | 37° C. overnight | 6.9% |
| WA802 | 1.5:1 | 37° C. overnight | 27.5% |
| WA802 | 1.5:1 | 37° C. overnight | 14.3% |
| WA802 | 1.5:1 | 37° C. overnight | 19.0% |
| WA802 | 200.0:1 | 37° C. overnight | 16.3% |

Other TNF's can be made using the systems we have described above. For example, we have constructed an hTNF derivative which lacks the first two amino acids of mature TNF, -val-arg-, and starts with -met-ser- when it is expressed in E.coli. This derivative is called pBR322-pL-T4 Δ2 hTNF. Its structure is otherwise the same as the pBR322-pL-T4 hTNF described above (FIG. 13).

To construct pBR322-pL-T4 Δ2hTNF, we made a synthetic linker fragment:

```
5'                                        AvaI
  CGAT ACT ATG AGC AGC AGT CGT ACC
      TAT GAT ACT CGT CGT CAGC AT GGGGCT
ClaI
```

We ligated this fragment to the larger ClaI-HindII fragment obtained from pBR322-pL-T4 hTNF (FIG. 13) in the presence of the 578 bp AvaI-HindIII fragment described above.

All of the above-described constructions pBR322-pL-T4-hTNF 153-pL-T4-hTNF-CA3(13), 153-pL-T4-hTNF-CA3-cts-T4ter and 153-T4-hTNF CA5-T4ter have an ATG start coden fused directly to the initial valine codon that begins mature human TNF (see FIGS. 13, 17 and 19). pBR322-pL-T4-Δ2-hTNF has an ATG codon fused to the initial serine codon of Δ2-TNF. Accordingly, the product produced by these constructions is likely Met-mature hTNF (or in the case of pBR322-pL-T4-Δ2-hTNF, Met-Δ2-hTNF). However, the N-terminal methionine may be cleaved by the E.coli during growth or production, or it may be, if necessary or desired, cleaved subsequently from the produced protein using available enzymes and cleavage techniques.

It should, of course, be understood that other TNF producing constructions and hosts could also have been employed in accordance with the processes of this invention. For example, any of the expression vectors and prokaryotic and eukaryotic hosts described previously could be used without departing from the scope of this invention. Moreover, the DNA sequences encoding the TNF-like polypeptides of this invention could be modified to improve their expression or product purification characteristics. For example, chemically or enzymatically prepared oligonucleotides could be inserted in front of the initiation codon of the TNF-like polypeptide, or used to replace codons at the N-terminal end of the DNA sequence coding for that polypeptide. By this procedure a more optional primary and higher order structure of the mRNA could be obtained. More specifically, a sequence can be so designed that the initiating AUG codon occurs in a readily accessible position (i.e., not masked by secondary structure) either at the top of the hair pin or in other signal-stranded regions. In addition, the position and sequences of the Shine-Dalgarno segment can likewise be optimized. The importance of such structural modifications is described, for example in D. Iserentant and W. Fiers, "Secondary Structure Of mRNA And Efficiency Of Translation Initiation", Gene, 9, pp. 1–12 (1980)).

Further increases in the cellular yield of the TNF-like polypeptides of this invention may be achieved by increasing the number of genes that can be utilized in a cell, e.g., by using high copy plasmids. See, e.g., B. Uhlin et al., "Plasmids With Temperature-Dependent Copy Number For Amplification Of Cloned Genes And Their Products", Gene, 6, pp. 91–106 (1979).

Therefore, it should be understood that the various TNF-related DNA sequences of this invention may be removed from the vectors described herein and placed in other vectors and hosts to improve the ultimate production of the products coded for by them.

It should also be understood that the TNF-like polypeptides of this invention may also include products in the form of fused proteins (e.g., linked to a prokaryotic, eukaryotic or combination N-terminal segment to direct excretion, improve stability, improve purification or improve possible cleavage of the N-terminal methionine or other N-terminal segment), in the form of pre-TNF (e.g., starting with part or all of the pre-sequence of a mammalian TNF or other eukaryotic or prokaryotic signal sequence), in the form of a mature TNF-like polypeptide, or in the form of an f-met-TNF-like polypeptide.

One particularly useful form of a TNF-like polypeptide of this invention, or at least a precursor thereof, would be mature TNF with an easily cleaved amino acid or series of amino acids attached to its N-terminus. Such construction would allow synthesis of the protein in an appropriate prokaryotic or eukaryotic host, where a start signal not present in mature TNF is required, and then cleavage in vivo or in vitro of the extra amino acids to produce mature TNF. Such methods exist. See, e.g., U.S. Pat. Nos. 4,332,892, 4,338,397, 4,366,346 and 4,425,437.

The TNF-polypeptides of this invention also include TNF-like polypeptides that are coded on expression by DNA sequences characterized by different codons for some or all of the codons of the described DNA sequences. These substituted codons may code for amino acids identical to those coded for by the codons replaced. Alternatively, the replacement or deletion of one or a combination of codons leading to one or more amino acid changes or to a larger or shorter TNF-like polypeptide that may alter the properties of the produced compound in a useful way (e.g., increase the stability, increase the solubility, increase the therapeutic activity or increase the half-life) are part of this invention.

Example 13: Activity of combinations of TNF and actinomycin D in vivo

We demonstrated the effect of the combination of r-hTNF and clinically acceptable dosages of actinomycin D on the growth rate of tumors in vivo. We injected three groups, eight per group, of nude mice subcutaneously with $5 \times 10^6$ JAMA (ovarian carcinoma) cells/mouse and allowed the tumors to grow for seven days. Group I received a daily intralesional ("i.l.") injection of $1 \times 10^5$ U of r-hTNF, alone; group II received the same daily dosage of r-hTNF, in combination with 0.3µg of actinomycin D, both i.l.; group III received the same daily dosage of r-hTNF (i.l.) in combination with 0.3µg of actinomycin D injected intraperitoneally ("i.p."). Our control group of eight mice received no treatment (group IV). Finally, a group of six mice (group V) received a daily dose of 0.3µg of actinomycin D per mouse, alone; three mice were injected i.l. and three mice were injected j.p.

We continued the daily injections for a period of three weeks. Each tumor was measured daily, prior to treatment. As indicated in FIGS. 18 and 19 we observed a pronounced tumor growth inhibition and even tumor regression in Group II, which we had treated with TNF and actinomycin D (i.l.). All other groups demonstrated tumor growth similar to that shown by the control group.

Microorganisms and recombinant DNA molecules prepared by the processes of this invention are exemplified by cultures deposited in the culture collection of the Deutsche Sammlung Von Mikroorganismen, in Gottingen, West Germany, on Dec. 17, 1984 (A and B) and Dec. 27, 1984 (C), and identified as TNF-A to C:

A. *E.coli* DH1 (λ) (p-mTNF-3) [DSM 3/59]

B. *E. coli* DH1 (λ) (p-hTNF-1) [DSM 3/60]

C. *E.coli* C600 (pBR322-pL-T4-hTNF) [DSM 3175]

In addition, the following microorganisms and recombinant DNA molecules were deposited in the culture collection of the Deutsche Sammlung Von Mikroorganisms on Aug. 29, 1985.

D. *E.coli* W3110 (153-pL-T4-CA3-cts-T4-ter) [DSM 3460]

E. *E.coli* W3110 (153-T4-CA5-T4-ter) [DSM 3461]

These deposits were assigned the following accession numbers: DSM 3460 and 3461, respectively.

The culture collection has assigned these deposits the following accession numbers DSM 3159, 3160 and 3175, respectively.

Having described our invention with particular reference to the preferred form thereof, it will be apparent to those skilled in the art to which the invention pertains that various changes and modifications may be made therein without departing from the spirit and scope of the invention as defined by the claims appended hereto.

We claim:

1. A recombinant DNA molecule characterized by a DNA sequence operatively linked to an expression control sequence selected from T4 or λpL-T4, said DNA sequence being selected from the group consisting of:

(a) the DNA insert of p-mTNF-3 (DSM 3159);

(b) the DNA insert of p-hTNF-1 (DSM 3160);

(c) DNA sequences that hybridize to one or both of the foregoing DNA inserts and which code on expression for a tumor necrosis factor; and (d) DNA sequences that code on expression for a polypeptide coded for on expression by any of the foregoing DNA inserts and sequences.

2. The recombinant DNA molecule according to claim 1, wherein the DNA sequence is selected from the group consisting of

AT GCT CAGAT CAT CT CT T CT CAAAAT T CGAGT G

ACAAGCCT GT AGCCCACGT CGT AGCAAACCAC

CAAGT GGAGGAGCAGCT GGAGT GGCT GAGCC

AGCGCGCCAACGCCCT CCT GGCCAACGGCAT G

GAT CT CAAAGACAACCAACT AGT GGT GCCAG

CCGAT GGGT T GT ACCT T GT CT ACT CCCAGGT T

CT CT T CAAGGGACAAGGCT GCCCCGACT ACG

T GCT CCT CACCCACACCGT CAGCCGAT T T GCT

AT CT CAT ACCAGGAGAAAGT CAACCT CCT CT

CT GCCGT CAAGAGCCCCT GCCCCAAGGACACC

CCT GAGGGGGCT GAGCT CAAACCCT GGT AT G

AGCCCAT AT ACCT GGGAGGAGT CT T CCAGCT G

GAGAAGGGGGACCAACT CAGCGCT GAGGT CA

AT CT GCCCAAGT ACT T AGACT T T GCGGAGT CC

GGGCAGGT CT ACT T T GGAGT CAT T GCT CT G and

CT CAGAT CAT CT T CT CAAAAT T CGAGT G

-continued

ACAAGCCT GT AGCCC ACGT CGT AGC AAACCA

CCAAGT GGAGGAGC AGCT GGAGT GGCT GAGCC

AGCGCGCC AACGCCCT CCT GGCC AACGGC AT

GGAT CT CAAAGAC AACC AACT AGT GGT GCC AG

CCGAT GGGT T GT ACCT T GT CT ACT CCC AGGT

TCT CTT CAAGGGAC AAGGCT GCCCC GACT ACG

T GCT CCT CACCC ACACC GT CAGCC GAT TT GC

TAT CT CAT ACC AGGAGA AAGT CAACCT CCT CT

CT GCC GT CAAGAGC CCCT GCCCC AAGGAC AC

CCCT GAGGGGGCT GAGCT CAAACCCT GGT AT G

AGCCC AT AT ACCT GGGAGGAGT CTT CCAGCT

GGAGAAGGGGGACC AACT CAGCGCT GAGGT CA

AT CT GCCC AAGT ACT T AGACT TT GCGGAGT C

CGGGC AGGT CT ACT TT GGAGT CATT GCT CT G.

3. The recombinant DNA molecule according to claim 1, wherein the DNA sequence is selected from the group consisting of

AT GGT CAGAT CAT CTT CT CGAACCCC GAGT G

ACAAGCCT GT AGCCC AT GTT GT AGCAAACCCT CAAGCT GAGGGGC AGCT CCAGT GGCT GAACC

GCC GGGCC AAT GCCCT CCT GGCC AAT GGCGT G GAGCT GAGAGAT AACC AGCT GGT GGT GCC AT

CAGAGGGCCT GT ACCT CAT CT ACT CCC AGGT C

CT CTT CAAGGGCC AAGGCT GCCCCT CC ACCC

AT GT GCT CCT CACCC ACACC AT CAGCC GCAT C

GCC GT CT CCT ACC AGACC AAGGT CAACCT CC

TCT CT GCC AT CAAGAGC CCCT GCC AGAGGGAG

ACCCC AGAGGGGGCT GAGGCC AAGCCCT GGT

AT GAGCCC AT CT AT CT GGGAGGGGT CTT CCAG

CT GGAGAAGGGT GACC GACT CAGCGCT GAGA

T CAAT CGGCCC GACT AT CT CGACT TT GCCGAG

TCT GGGC AGGT CT ACT TT GGGAT CATT GCCC

T G and GT CAGAT CAT CTT CT CGAACCCC GA

GT GACAAGCCT GT AGCCC AT GTT GT AGC AAA

CCCT CAAGCT GAGGGGC AGCT CCAGT GGCT GA

ACC GCC GGGCC AAT GCCCT CCT GGCC AAT GG

CGT GGAGCT GAGAGAT AACC AGCT GGT GGT GC

CAT CAGAGGGCCT GT ACCT CAT CT ACT CCC A

GGT CCT CTT CAAGGGCC AAGGCT GCCCCT CCA

CCC AT GT GCT CCT CACCC ACACC AT CAGCC G

CAT CGCC GT CT CCT ACC AGACC AAGGT CAACC

TCCT CT CT GCC AT CAAGAGC CCCT GCC AGAG

-continued

GGAGACCCC AGAGGGGGCT GAGGCC AAGCCCT

GGT AT GAGCCC AT CT AT CT GGGAGGGGT CTT

CC AGCT GGAGAAGGGT GACC GACT CAGCGCT G

AGAT CAAT CGGCCC GACT AT CT CGACT TT GC

CGAGT CT GGGC AGGT CT ACT TT GGGAT CATT G

CCCT G.

4. A recombinant DNA molecule selected from the group consisting of pBR322-pL-T4-hTNF (DSM 3175), pBR322-pL-T4-Δ2-hTNF, 153-pL-T4-hTNF-CA3-cts-T4ter (DSM 3460), and 153-T4-hTNF-CA5-T4ter (DSM 3461).

5. A process for producing a tumor necrosis factor polypeptide comprising the steps of culturing a prokaryotic host transformed with a recombinant DNA molecule selected from the group consisting of 153-pL-T4-hTNF-CA3(B), pBR322-pL-T4-hTNF (DSM 3175), pBR322-pL-T4-Δ2-hTNF, 153-pL-T4-hTNF-CA3-cts-T4ter (DSM 3460), and 153-T4-hTNF-CAS-T4ter (DSM 3461); and collecting said polypeptide.

6. The process according to claim 5, wherein the host is selected from strains of E.coli, Bacillus, Streptomyces, yeasts and other fungi.

7. The process according to claim 16, wherein the transformed host is selected from the group consisting of E coli W3110 (153-pL-T4-hTNF-CA3(13), E.coli W3110 (153-pL-T4-hTNF-CA3-cts-T4ter), E.coli W3110 (153-T4-hTNF-CA5-T4ter), and E.coli WA802 (153-T4-hTNF-CA5-T4ter).

8. A process for producing a tumor necrosis factor polypeptide comprising the steps of culturing a prokaryotic host transformed with a recombinant DNA molecule characterized by a DNA sequence operatively linked to an expression control sequence selected from T4 or λpL-T4, said DNA sequence being selected from the group consisting of

AT GCT CAGAT CAT CTT CT CAAAATT C

GAGT GACAAGCCT GT AGCCC ACGT CG

T AGC AAACC ACC AAGT GGAGGAGC AG

CT GGAGT GGCT GAGCC AGCGCGCC AA

CGCCCT CCT GGCC AACGGC AT GGAT C

T CAAAGAC AACC AACT AGT GGT GCC A

GCC GAT GGGT T GT ACCT T GT CT ACT C

CC AGGTT CT CTT CAAGGGAC AAGGCT

GCCCC GACT ACGT GCT CCT CACCC AC

ACC GT CAGCC GAT TT GCT AT CT CAT A

CC AGGAGA AAGT CAACCT CCT CT CT G

CCGT CAAGAGC CCCT GCCCC AAGGAC

ACCCCT GAGGGGGCT GAGCT CAAACC

CT GGT AT GAGCCC AT AT ACCT GGGAG

GAGT CTT CC AGCT GGAGAAGGGGGAC

CAACT CAGCGCT GAGGT CAAT CT GCC

CAAGT ACTT AGACT TT GCGGAGT CCG

GGCAGGTCTACTTTGGAGTCATTGCT

CTG and CTCAGATCATCTTCTCAA

AATTCGAGTGACAAGCCTGTAGCCCA

CGTCGTAGCAAACCACCAAGTGGAGG

AGCAGCTGGAGTGGCTGAGCCAGCGC

GCCAACGCCCTCCTGGCCAACGGCAT

GGATCTCAAAGACAACCAACTAGTGG

TGCCAGCCGATGGGTTGTACCTTGTC

TACTCCCAGGTTCTCTTCAAGGGACA

AGGCTGCCCCGACTACGTGCTCCTCA

CCCACACCGTCAGCCGATTTGCTATC

TCATACCAGGAGAAAGTCAACCTCCT

CTCTGCCGTCAAGAGCCCCTGCCCCA

AGGACACCCCTGAGGGGGCTGAGCTC

AAACCCTGGTATGAGCCCATATACCT

GGGAGGAGTCTTCCAGCTGGAGAAGG

GGGACCAACTCAGCGCTGAGGTCAAT

CTGCCCAAGTACTTAGACTTTGCGGA

GTCCGGGCAGGTCTACTTTGGAGTCA

TTGCTCTG;

and collecting said polypeptide.

9. A process for producing a tumor necrosis factor polypeptide comprising the steps of culturing a prokaryotic host transformed with a recombinant DNA molecule characterized by a DNA sequence operatively linked to an Expression control sequence selected from T4 or λpL-T4, said DNA sequence being selected from the group consisting of

ATGGTCAGATCATCTTCTCGAACCCCGAGTG

ACAAGCCTGTAGCCCATGTTGTAGCAAACCCT

CAAGCTGAGGGGCAGCTCCAGTGGCTGAACC

GCCGGGCCAATGCCCTCCTGGCCAATGGCGTG

GAGCTGAGAGATAACCAGCTGGTGGTGCCAT

CAGAGGGCCTGTACCTCATCTACTCCCAGGTC

CTCTTCAAGGGCCAAGGCTGCCCCTCCACCC

ATGTGCTCCTCACCCACACCATCAGCCGCATC

GCCGTCTCCTACCAGACCAAGGTCAACCTCC

TCTCTGCCATCAAGAGCCCCTGCCAGAGGGAG

ACCCCAGAGGGGGCTGAGGCCAAGCCCTGGT

ATGAGCCCATCTATCTGGGAGGGGTCTTCCAG

CTGGAGAAGGGTGACCGACTCAGCGCTGAGA

TCAATCGGCCCGACTATCTCGACTTTGCCGAG

TCTGGGCAGGTCTACTTTGGGATCATTGCCC

TG and GTCAGATCATCTTCTCGAACCCCGA

GTGACAAGCCTGTAGCCCATGTTGTAGCAAA

CCCTCAAGCTGAGGGGCAGCTCCAGTGGCTGA

ACCGCCGGGCCAATGCCCTCCTGGCCAATGG

CGTGGAGCTGAGAGATAACCAGCTGGTGGTGC

CATCAGAGGGCCTGTACCTCATCTACTCCCA

GGTCCTCTTCAAGGGCCAAGGCTGCCCCTCCA

CCCATGTGCTCCTCACCCACACCATCAGCCG

CATCGCCGTCTCCTACCAGACCAAGGTCAACC

TCCTCTCTGCCATCAAGAGCCCCTGCCAGAG

GGAGACCCCAGAGGGGGCTGAGGCCAAGCCCT

GGTATGAGCCCATCTATCTGGGAGGGGTCTT

CCAGCTGGAGAAGGGTGACCGACTCAGCGCTG

AGATCAATCGGCCCGACTATCTCGACTTTGC

CGAGTCTGGGCAGGTCTACTTTGGGATCATTG

CCCTG;

and collecting said polypeptide.

10. The recombinant DNA molecule 153-T4-hTNF-CA5-T4ter (DSM 3461).

11. A process for producing a tumor necrosis factor comprising the step of culturing a prokaryotic host transformed with a recombinant DNA molecule as defined in claim 10 and collecting said tumor necrosis factor.

* * * * *